US009725701B2

(12) United States Patent
McLaren et al.

(10) Patent No.: US 9,725,701 B2
(45) Date of Patent: Aug. 8, 2017

(54) PROKARYTOIC-TYPE ISOCITRATE DEHYDROGENASE AND ITS APPLICATION FOR IMPROVING NITROGEN UTILIZATION IN TRANSGENIC PLANTS

(71) Applicant: Iowa Corn Promotion Board, Johnston, IA (US)

(72) Inventors: James McLaren, Chesterfield, MO (US); Brian Vande Berg, Morrisville, NC (US)

(73) Assignee: Iowa Corn Promotion Board, Johnston, IA (US)

( * ) Notice: Subject to any disclaimer, the term of this patent is extended or adjusted under 35 U.S.C. 154(b) by 966 days.

(21) Appl. No.: 13/833,247

(22) Filed: Mar. 15, 2013

(65) Prior Publication Data

US 2014/0283224 A1    Sep. 18, 2014

(51) Int. Cl.
*C12N 15/29* (2006.01)
*C12N 15/82* (2006.01)
*C12N 9/04* (2006.01)

(52) U.S. Cl.
CPC ....... *C12N 9/0006* (2013.01); *C12N 15/8261* (2013.01)

(58) Field of Classification Search
None
See application file for complete search history.

(56) References Cited

U.S. PATENT DOCUMENTS

| | | | |
|---|---|---|---|
| 6,121,513 A | 9/2000 | Zhang et al. | |
| 6,204,039 B1* | 3/2001 | Allen | C12N 9/0006 435/190 |
| 6,562,958 B1 | 5/2003 | Breton et al. | |
| 6,673,910 B1 | 1/2004 | Breton | |
| 6,995,250 B1 | 2/2006 | Hirano et al. | |
| 7,214,786 B2 | 5/2007 | Kovalic et al. | |
| 7,504,111 B2 | 3/2009 | Fontana et al. | |
| 7,517,684 B2 | 4/2009 | Rubenfield et al. | |
| 7,569,389 B2 | 8/2009 | Feldmann et al. | |
| 7,630,836 B2 | 12/2009 | Omura et al. | |
| 7,777,097 B2 | 8/2010 | Glazebrook et al. | |
| 7,862,827 B2 | 1/2011 | Giuliani et al. | |
| 7,867,704 B2 | 1/2011 | Kapur et al. | |
| 8,247,650 B2 | 8/2012 | Hershey et al. | |
| 2011/0252503 A1* | 10/2011 | McLaren | C12N 9/1217 800/278 |

FOREIGN PATENT DOCUMENTS

| | | |
|---|---|---|
| CN | 101421295 | 4/2009 |
| CN | 102711445 | 10/2012 |
| WO | 9928479 | 6/1999 |
| WO | 2011056769 | 5/2011 |

OTHER PUBLICATIONS

Lemaitre et al. (Plant Physiology, Jul. 2007, vol. 144, pp. 1546-1558).*
Sahara et al. (Biosci. Biotechnol. Biochem. 66:489-500(2002)).*
Guo et al (2004, Proc. Natl. Acad. Sci. USA 101: 9205-9210).*
Liu et al. (J. Plant Biol. (2010) 53:107-112).*
Chen, Ridong, "Plant NADP-Dependent Isocitrate Dehydrogenases are Predominantly Localized in the Cystol", "Planta", 1998, pp. 280-285, vol. 207, Published in: US.
Foyer, C. et al., "Respiration and Nitrogen Assimilation: Targeting Mitochodria-associates Metabolism as a Means to Enhance Nitrogen Use Efficiency", "Journal of Experimental Biology", 2011, pp. 1467-1482, vol. 62, No. 4.
Igamberdiev, A. et al., "Regulation of NAD- and NADP-dependent Isocitrate Dehydrogenases by Reduction Levels of Pyridine Nucleotides in Mitochondria and Cytosol of Pea Leaves", "Biochim Biophys Acta", Sep. 30, 2003, pp. 117-125, vol. 1606.
Leterrier, M. et al., "Cytosolic NADP-Isocitrate Dehydrogenase of Pea Plants: Genomic Clone Characterization and Fuctional Analysis Under Abiotic Stress Conditions", "Free Radical Research", Feb. 1, 2007, pp. 191-199, vol. 41, No. 2.
Sienkiewicz-Porzucek, A. et al., "Mild Reductions in Mitochondrial NAD-Dependent Isocitrate Dehydrogenase Activity Result in Altered Nitrate Assimaltion and Pigmentation But Do Not Impact Growth", "Molecular Plant", 2009, pp. 156-173, vol. 3, No. 1.
Sahara et al., "Cloning, Sequencing, and Expression of a Gene Encoding the Monomeric Isocitrate Dehydrogenase of the Nitrogen-fixing Bacterium", 2002, pp. 589-500, vol. 66, No. 3, Publisher: Bioscience Biotechnology Biochemistry, Published in: Sapporo, Japan.
Sahara et al., "Isocitrate dehydrogenase", "GenBank Abstract", Jul. 27, 2011.
Popova et al., "Citrate and isocitrate in plant metabolism", "Biochimica et Biophysica Ada", May 27, 1998, pp. 307-325, vol. 1364, No. 3, Published in: NL.
Anonymous, "UNIPROT:P16100", "http://bis/exam/dbfetch.jsp?id=UNIPROTP16100", Jan. 23, 2007.

* cited by examiner

*Primary Examiner* — Shubo (Joe) Zhou
*Assistant Examiner* — Charles Logsdon
(74) *Attorney, Agent, or Firm* — Davis, Brown, Koehn, Shors & Roberts, P.C.; Kent A. Herink; Matthew W. Coryell

(57) ABSTRACT

The present invention relates to transgenic plants that have increased nitrogen use efficiency, stress tolerance, and/or alleviating a limitation such that yield is increased, or a combination of these and that have been transformed using a novel vector construct including a synthetic isocitrate dehydrogenase (icdh) gene that modulates nitrogen use in plants. The invention also relates to stacking the icdh gene with other exogenous or heterologous genes that modulate nitrogen use in the plant, including a N-acetylglutamate kinase gene. The invention also relates to methods of expressing in plants the nucleic acid molecules corresponding to the nucleic acid sequences that modulate nitrogen use in plants or are modulated by nitrogen conditions.

23 Claims, 2 Drawing Sheets

PROKARYOTIC-TYPE ISOCITRATE DEHYDROGENASE AND ITS APPLICATION FOR IMPROVING NITROGEN UTILIZATION IN TRANSGENIC PLANTS

REFERENCE TO THE SEQUENCE LISTING

Applicant hereby incorporates by reference material submitted via Web-EFS in the following file:

| File Name | Date Created | Size |
|---|---|---|
| 13-833247_5T25.txt | August 27, 2013 | 16 kb |

FIELD OF THE INVENTION

The invention relates generally to plants with improved nitrogen utilization and stress tolerance, more specifically, to heterologous expression of an isocitrate dehydrogenase (ICDH) enzyme in plants, including the overexpression and characterization of a prokaryotic-based isocitrate dehydrogenase that improves stress tolerance and nitrogen uptake, metabolism or both. The invention also includes stacking of the icdh gene with one or more other transgenes to improve nitrogen utilization and/or stress tolerance.

BACKGROUND OF THE INVENTION

Plants require nitrogen during their vegetative and reproductive growth phases. Nitrogen is made available to the plant through soil mineralization, the application of nitrogen fertilizer, or both. It has been estimated, however, that between 50 and 70 percent of nitrogen applied to crops is lost from the plant-soil system [Peoples, M. B. et al., "Minimizing Gaseous Losses of Nitrogen," In *Nitrogen Fertilizer in the Environment* (Bacon, P. E., ed.) Marcel Dekker, pp. 565-606 (1995)]. Nitrogen is one of the most expensive plant nutrients to supply, nitrogen fertilizer is not always available at a reasonable cost, and excessive application of nitrogen fertilizer can result in environmental challenges. Corn is an example of an agronomically important plant that often requires nitrogen fertilizers to perform at its genetic potential.

Native ICDH can exist in the mitochondria, chloroplast and cytosol, with each having a different physiological impact although the catalytic action may be similar. In general, ICDH1 is found in the cytosol and ICDH2 is found in the chloroplast.

For co-factor reducing power, ICDH can use either nicotinamde adenine dinucleotide (NAD+) or nicotinamde adenine dinucleotide phosphate (NADP+), depending on which metabolic pathway it is active. Some publications indicate that the main function of ICDH may be to generate reducing power (NADH, NADPH) for other metabolic reactions, for example, in the β-oxidation of unsaturated fatty acids. Other theories include the suggestion that the reaction product, 2-oxyglutarate (OG), could be used to support amino acid synthesis via the GOGAT cycle (Hodges, M. Enzyme redundancy and the importance of 2-oxoglutarate in plant ammonium assimilation. J. Exp. Botany (2002), 53, 905). In addition, the over-expression of the ICDH enzyme in a stack with another gene or genes may allow the effective utilization of the additional carbon skeletons. A previous study of transgenic tobacco plants that overexpressed a mitochondrial icdh gene was focused on redox pathways and did not mention nor evaluate any possible impact on nitrogen utilization (Gray, G., Villarimo, A., Whitehead, C., McIntosh, L. Transgenic Tobacco (*Nicotiana tabacum* L.) Plants with Increased Expression Levels of Mitochondrial NADP+-dependent Isocitrate Dehydrogenase: Evidence Implicating this Enzyme in the Redox Activation of the Alternative Oxidase, *Plant and Cell Physiology* 2004; 45, 1413-1425).

Regulation of NAD- and NADP-dependent isocitrate dehydrogenases (NAD-ICDH, EC 1.1.1.41 and NAD-P_ICDH, EC 1.1.1.42) is complex due to expression, substrates, compartments and post-translational regulation. While it is unclear which ICDH version generates OG for amino acids, any such OG would have to be in, or enter, the chloroplast where nitrogen is assimilated into amino acids. The literature suggests that plant cytostolic versions of ICDH are homodimers with subunits of approximately 47 kD. Mitochondrial ICDH is suspected to have more subunits. Bacterial versions of ICDH may be monomeric and have been considered to overcome the typical regulation of expression and function that occurs with plant ICDH in plants, that is, phosphorylation may inactivate the homodimer.

Cytostolic NADP-specific ICDH catalyzes the conversion of citrate to oxoglutarate. One strategy is to design a construct containing a gene encoding a monomeric prokaryotic-type isocitrate dehydrogenase gene (icdh), and to direct overexpression of ICDH in the cytoplasm of plants. The expressed ICDH enzyme will enhance the plant's ability to utilize available nitrogen via an enhanced flow of carbon into the nitrogen assimilatory mechanism. Here, we describe the overexpression and characterization of asynthetic icdh gene based on selection from among bacterial icdh sequences and optimized for expression in corn, and the stacking of a icdh genes with other transgenes.

SUMMARY OF THE INVENTION

The present invention relates to transgenic plants that have increased nitrogen use efficiency, stress tolerance, or both, that have been transformed using a novel vector construct including an icdh nucleic acid sequence that modulates nitrogen use in plants. A variety of icdh nucleic acid sequences were identified for use with the present invention from the several bacterial and plant genomic sequencing projects that have been archived in public databases from which sequences that encode ICDH enzymes with robust activity could be selected. These candidate icdh sequences were then screened to deselect those that had a relatively high content of poly A regions, which can be inhibitory to expression in plants. The sequence chosen to exemplify these icdh sequences was then codon-optimized for expression in maize (SEQ ID No 1). The invention also includes stacking an icdh gene with one or more heterologous genes so as to induce the over-expression of the ICDH enzyme in combination with nitrogen assimilatory enzymes. The invention also relates to isolated vectors for transforming plants and to antibodies for detecting expression of the nucleotide sequence(s) of interest in the transformed plants. The invention also relates to methods of expressing in plants the nucleic acid molecules corresponding to the nucleic acid sequences that modulate nitrogen use in plants.

Specifically, vectors for transforming plants and bacterial cells have been constructed using the nucleotide sequences SEQ ID NO: 1 and 3, as well as combinations, variants, fragments, and complements thereof. These vectors include a 5' DNA promoter sequence and a 3' terminator sequence, wherein the nucleic acid sequence, the DNA promoter sequence, and the terminator sequence are operatively coupled to permit transcription of the nucleotide sequence. In some embodiments, the promoter sequence may be a constitutive plant promoter or a tissue specific promoter.

The invention also includes polyclonal antibodies, comprising polyclonal antibodies to a polypeptide encoded by nucleotide sequences SEQ ID NO: 1 and 3 and combinations thereof.

The invention also includes plants transformed with a nucleotide sequences SEQ ID NO: 1 and 3, as well as combinations, variants and fragments thereof. The plant is selected from the group consisting of corn (maize), sorghum, wheat, sunflower, tomato, crucifers, peppers, potato, cotton, rice, soybean, sugarbeet, sugarcane, tobacco, barley, and oilseed rape, Brassica sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, grasses (such as turf grasses, forage grasses, or pasture grasses), ornamentals, trees (such as fruit trees, nut trees, pulp trees, oil palms) and conifers. The invention also includes a component part of such plants, plant seed produced from such plants, and a plant seed transformed with a vector construct of the present invention.

The invention also includes a host cell transformed with a nucleotide sequence selected from SEQ ID NO: 1 and 3, and combinations thereof. The host cell may be a bacterial cell or a plant cell.

The invention also includes a method of expressing a nucleic acid molecule that modulates nitrogen in a plant, said method comprising the steps of providing a transgenic plant or plant seed transformed with a vector construct according to the present invention, and growing the transgenic plant or a plant grown from the transgenic plant seed under conditions effective to express the nucleic acid molecule in said transgenic plant or said plant grown from the transgenic plant seed. Growing of the transgenic plant is effective in increasing nitrogen uptake of said transgenic plant or said plant grown from the transgenic plant seed, and/or in increasing efficiency of nitrogen utilization of said transgenic plant or said plant grown from the transgenic plant seed, and/or alleviating a limitation such that yield is increased in said transgenic plant or said plant grown from the transgenic plant seed. The invention also includes the foregoing methods wherein a transgenic plant is provided or a transgenic seed is provided. The invention also includes the foregoing method wherein the plant is selected from the group consisting of corn (maize), sorghum, wheat, sunflower, tomato, crucifers, peppers, potato, cotton, rice, soybean, sugarbeet, sugarcane, tobacco, barley, and oilseed rape, Brassica sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, grasses (such as turf grasses, forage grasses, or pasture grasses), ornamentals, trees (such as fruit trees, nut trees, pulp trees, oil palms) and conifers.

The invention also includes a method of improving the stress tolerance of a plant by expressing a nucleic acid molecule modulated by nitrogen in a plant, said method comprising the steps of providing a transgenic plant or plant seed transformed with a vector construct according to the present invention and growing the transgenic plant or a plant grown from the transgenic plant seed under conditions effective to express the nucleic acid molecule in said transgenic plant or said plant grown from the transgenic plant seed.

The invention also includes a method of altering the morphology of a plant by expressing a nucleic acid molecule modulated by nitrogen in a plant, said method comprising the steps of providing a transgenic plant or plant seed transformed with a vector construct according to the present invention and growing the transgenic plant or a plant grown from the transgenic plant seed under conditions effective to express the nucleic acid molecule in said transgenic plant or said plant grown from the transgenic plant seed.

The invention also includes a vector construct, comprising a nucleotide sequence encoding the ICDH amino acid sequence including SEQ ID NO: 2 and 4, and combinations thereof, a 5' DNA promoter sequence, and a 3' terminator sequence, wherein the nucleotide sequence, the DNA promoter sequence, and the terminator sequence are operatively coupled to permit transcription of the nucleotide sequence.

The invention also includes a vector construct comprising a nucleotide sequence that modulates nitrogen in a plant, wherein said nucleotide sequence is selected from SEQ ID NO: 1 and 3, and combinations thereof; a nucleotide sequence having at least 85% sequence identity to the corresponding nucleotide sequence of SEQ ID NO: 1 and 3, and combinations thereof, wherein said nucleotide sequence modulates nitrogen in a plant; a nucleotide sequence selected from those encoding the ICDH amino acid sequences SEQ ID NO: 2 and 4, and combinations thereof; and, a nucleotide sequence encoding an amino acid sequence having at least 85% sequence identity to the amino acid sequence of SEQ ID NO: 2 and 4, and combinations thereof; wherein said nucleotide sequence modulates nitrogen in a plant, wherein said construct further comprises a 5' DNA promoter sequence and a 3' terminator sequence, wherein the nucleotide sequence, the DNA promoter sequence, and the terminator sequence are operatively coupled to permit transcription of the nucleotide sequence.

DETAILED DESCRIPTION OF PREFERRED EMBODIMENTS

Figure 1:
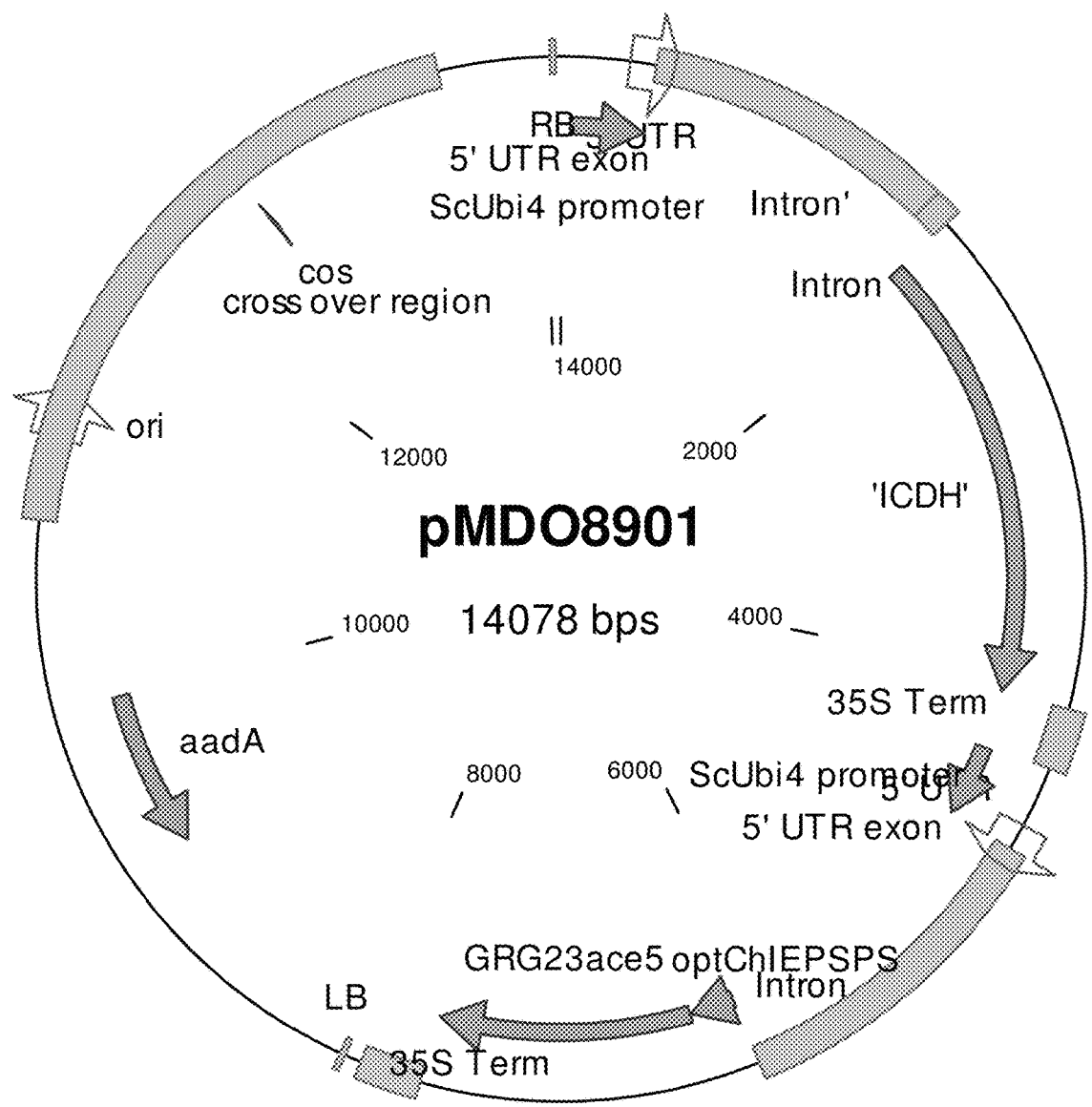
FIG. 1 is a vector map for the plasmid pMDO8901, wherein the Main elements in the plasmid (clockwise from top) are: Right Border, ScUbi4 promoter, 5' UTR exon, intron, icdh gene, 35S terminator, ScUbi4 promoter, 5' UTR exon, intron, chloroplast transit peptide from EPSPS, nagk gene, 35S terminator, ScUbi4 promoter, 5' UTR exon, intron, chloroplast transit peptide from EPSPS, glyphosate tolerance SM (GRG23ac35), 35S terminator, Left Border.

The development of plant varieties that use nitrogen more efficiently will reduce the need for excessive inputs of nitrogen, save production costs for farmers, benefit farmers in developing countries who do not have access to fertilizer inputs, and reduce environmental contamination associated with the application of excessive nitrogen fertilizers. One approach that has been used in the development of plant varieties with improved nitrogen utilization relies on conventional plant breeding techniques. However, such approaches have had variable success due to lack of specification in the genetic recombination.

There is a need to develop plant cultivars that absorb and use nitrogen more efficiently. Plant scientists have adopted the shorthand term nitrogen use efficiency (NUE), and a variety of methods of measuring and evaluating NUE have been developed [Craswell, E. T. and Godwin, D. C. (1984) The efficiency of nitrogen fertilizers applied to cereals grown in different climates. In *Advances in Plant Nutrition* (Vol. 1) (Tinker, P. B. and Lauchli, A., eds), pp. 1-55, Praeger Publishers; Steenbjerg, F. and Jakobsen, S. T. (1963) Plant nutrition and yield curves. *Soil Sci.* 95, 69-90; Siddiqi, M. Y. and Glass, D. M. (1981) Utilization index: a modified approach to the estimation and comparison of nutrient utilization efficiency in plants. *J. Plant Nutr.* 4, 289-302; Moll, R. H. et al. (1982) Analysis and interpretation of factors which contribute to efficiency of nitrogen utilization. *Agron. J.* 74, 562-564]. There are differences in the specific definitions, and context of use. For example, some definitions are based on total biomass while others are based on the weight of grain yielded. Another set of definitions uses the efficiency of extracting nitrogen from the soil. The efficiency with which applied nitrogen is used to improve grain yield may be measured by agronomic efficiency (AE), the product of physiological efficiency and utilization efficiency, or NUEg which is the product of uptake efficiency and utilization efficiency. Other definitions take physiological factors into account.

As used in this specification, the term nitrogen use efficiency, or NUE, is defined to include a measurable change in any of the main nitrogen metabolic pool sizes in the assimilation pathways (for example, may include a measurable change in one or more of the following: nitrate, nitrite, ammonia, glutamic acid, aspartic acid, glutamine, asparagine, lysine, leucine, threonine, methionine, glycine, tryptophan, tyrosine, total protein content of a plant part, total nitrogen content of a plant part, and/or chlorophyll content), or where the plant is shown to provide the same or elevated biomass or harvestable yield at lower nitrogen fertilization levels, or where the plant is shown to provide elevated biomass or harvestable yields at the same nitrogen fertilization levels when compared to a plant that has not been transformed with a nitrogen-modulating nucleic acid construct of the invention. A "measurable change" can include an increase or a decrease in the amount of any component ("metabolic pool") of the nitrogen assimilation pathway. A change can include either a decrease or an increase in one or more metabolic pools in the pathway, or a decrease in one or more pools with a concomitant increase in one or more other pool(s), such as when one intermediate in the nitrogen assimilation pathway is being utilized for the purpose of generating another intermediate or product of the pathway. For example, in the conversion of glutamate to glutamine, the level of glutamate may decrease while the level of glutamine may increase. Thus, while not being bound by any particular theory or mechanism, any change in one or more of these pools indicates that nitrogen is being utilized more efficiently by the plant.

An increase in nitrogen utilization efficiency can be associated with about a 5%, about a 10%, 15%, 20%, 30%, 40%, 50%, 60%, 70%, 80%, 90%, 100%, 125%, 150%, about a 200% or greater measurable change in any of the main nitrogen metabolic pool sizes in the assimilation pathway. In one embodiment, the transgenic plants of the invention have an increased nitrogen uptake from the environment when compared to a plant that does not contain a nitrogen-modulating sequence of the invention. By "nitrogen modulating sequence" it is intended to mean a nucleotide or amino acid sequence that modulates NUE, by way of non-limiting example: either by generating an enzyme that impacts NUE, or by generating a protein that interacts with the components involved in NUE, or by generating a protein that impacts the internal homeostatic signal cascade regulating NUE, or by a combination of these mechanisms that results in a measurable change in N uptake, N assimilation, N metabolism, N transport, N utilization, N storage, or a combinations of these. The present invention further provides a method of improving stress tolerance in a plant by expressing one or more nitrogen-modulating nucleotide sequences within the plant. In one embodiment, the nitrogen-modulating nucleotide sequence is SEQ ID NO: 1, or variants and fragments thereof. In another embodiment, the nitrogen-modulating nucleotide sequence is a nucleotide sequence that encodes SEQ ID NO: 2, or variants and fragments thereof. In another embodiment, the nitrogen-modulating nucleotide sequence is a nucleotide sequence that encodes SEQ ID NO 1 plus SEQ ID NO: 2, or variants and fragments thereof, respectively.

As used herein, the term "stress" or "stress condition" refers to the exposure of a plant, plant cell, or the like, to a physical, environmental, biological or chemical agent or condition that has an adverse effect on metabolism, growth, development, propagation and/or survival of the plant (collectively "growth"). A stress can be imposed on a plant due, for example, to an environmental factor such as water (e.g., flooding, drought, dehydration), anaerobic conditions (e.g., a low level of oxygen), abnormal osmotic conditions, salinity or temperature (e.g., hot/heat, cold, freezing, frost), a deficiency of nutrients such as nitrogen, phosphate, potassium, sulfur, micronutrient, or exposure to pollutants, or by a hormone, second messenger or other molecule. Anaerobic stress, for example, is due to a reduction in oxygen levels (hypoxia or anoxia) sufficient to produce a stress response. A flooding stress can be due to prolonged or transient immersion of a plant, plant part, tissue or isolated cell in a liquid medium such as occurs during monsoon, wet season, flash flooding or excessive irrigation of plants, or the like. A cold stress or heat stress can occur due to a decrease or increase, respectively, in the temperature from the optimum range of growth temperatures for a particular plant species. Such optimum growth temperature ranges are readily determined or known to those skilled in the art. Dehydration stress can be induced by the loss of water, reduced turgor, or reduced water content of a cell, tissue, organ or whole plant. Drought stress can be induced by or associated with the deprivation of water or reduced supply of water to a cell, tissue, organ or organism. Saline stress (salt stress) can be associated with or induced by a perturbation in the osmotic potential of the intracellular or extracellular environment of a cell. Osmotic stress also can be associated with or induced by a change, for example, in the concentration of molecules in the intracellular or extracellular environment of a plant cell, particularly where the molecules cannot be partitioned across the plant cell membrane.

An improvement in stress tolerance can be assessed by any quantitative or qualitative measure of plant performance under a given stress condition and is relative to the performance of a plant grown under the same stress conditions that has not been transformed with a nitrogen-modulating sequence of the invention. Thus, the plants may exhibit improved nitrogen contents, altered amino acid or protein compositions, altered carbohydrate composition, altered oil composition, vigorous growth characteristics, increased vegetative yields or better seed yields and qualities. These plants may be identified by examining any of following parameters: 1) the rate of growth, measured in terms of rate of increase in fresh or dry weight; 2) vegetative yield of the mature plant, in terms of fresh or dry weight; 3) the seed or fruit yield; 4) the seed or fruit weight; 5) the total nitrogen content of the plant; 6) the total nitrogen content of the fruit or seed; 7) the free amino acid content of the plant; 8) the free amino acid content of the fruit or seed; 9) the total protein content of the plant; 10) the total protein content of the fruit or seed; 11) measurable change in carbohydrates or oils. The procedures and methods for examining these parameters are well known to those skilled in the art. These methods may involve enzymatic assays and immunoassays to measure enzyme/protein levels; assays to measure the amino acid composition, free amino acid pool or total nitrogen content of various plant tissues; measurement of growth rates in terms of fresh weight gains over time; or measurement of plant yield in terms of total dry weight and/or total seed weight.

Transformation of Bacterial or Plant Cells

Provided herein are novel nucleotide sequences that modulate nitrogen utilization efficiency in plants. Also provided are amino acid sequences of the proteins of the invention, that may be nitrogen-modulating or modulated by nitrogen concentration.

The nitrogen-modulating nucleotide sequences of the invention may be modified to obtain or enhance expression in plant cells. The nitrogen-modulating sequences of the invention may be provided in expression cassettes for expression in the plant of interest. "Plant expression cassette" includes DNA constructs that are capable of resulting in the expression of a protein from an open reading frame in a plant cell. The cassette will include in the 5'-3' direction of transcription, a transcriptional initiation region (i.e., promoter) operably-linked to a DNA sequence of the invention, and a transcriptional and translational termination region (i.e., termination region) functional in plants. The cassette may additionally contain at least one additional gene to be co-transformed into the organism, such as a selectable marker gene or a stacked gene of different function. Alternatively, the additional gene(s) can be provided on multiple expression cassettes. Such an expression cassette is provided with a plurality of restriction sites for insertion of the nitrogen-modulating sequence to be under the transcriptional regulation of the regulatory regions.

By "promoter" is intended a nucleic acid sequence that functions to direct transcription of a downstream coding sequence. The promoter, together with other transcriptional and translational regulatory nucleic acid sequences (also termed as "control sequences"), are necessary for the expression of a DNA sequence of interest. Preferably, the promoter is one that is known to stimulate transcription in the organism into which the nucleotide sequence of the invention is being introduced.

The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention. "Heterologous" generally refers to the nucleic acid sequences that are not endogenous to the cell or part of the native genome in which they are present, and have been added to the cell by infection, transfection, microinjection, electroporation, microprojection, or the like. By "operably linked" is intended a functional linkage between a promoter and a second sequence, wherein the promoter sequence initiates and mediates transcription of the DNA sequence corresponding to the second sequence. Generally, "operably linked" means that the nucleic acid sequences being linked are contiguous, including exons and introns and, where necessary to join two protein coding regions, contiguous and in the same reading frame.

In one embodiment, the promoter is a constitutive promoter. Suitable constitutive promoters for use in plants include: the promoters from plant viruses, such as the peanut chlorotic streak caulimovirus (PC1SV) promoter (U.S. Pat. No. 5,850,019); the 35S promoter from cauliflower mosaic virus (CaMV) (Odell et al. (1985) *Nature* 313:810-812); promoters of *Chlorella* virus methyltransferase genes (U.S. Pat. No. 5,563,328) and the full-length transcript promoter from figwort mosaic virus (FMV) (U.S. Pat. No. 5,378,619); the promoters from such genes as rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689), including the TrpPro5 promoter (U.S. patent application Ser. No. 10/377,318; filed Mar. 16, 2005); pEMU (Last et al. (1991) *Theor. Appl. Genet.* 81:581-588); MAS (Velten et al. (1984) *EMBO J.* 3:2723-2730); maize H3 histone (Lepetit et al. (1992) *Mol. Gen. Genet.* 231:276-285 and Atanassova et al. (1992) *Plant J.* 2(3):291-300); *Brassica napus* ALS3 (PCT application WO 97/41228); and promoters of various *Agrobacterium* genes (see U.S. Pat. Nos. 4,771,002; 5,102,796; 5,182,200; and 5,428,147).

In another embodiment, the promoter is a tissue-specific promoter. A list of commonly-used tissue-specific promoters can be found in Reviewed in Moore et al. (2006) *Plant J.* 45(4):651-683, which is herein incorporated by reference in its entirety.

Often, such constructs will also contain 5' and 3' untranslated regions. Such constructs may contain a "signal sequence" or "leader sequence" to facilitate co-translational or post-translational transport of the peptide of interest to certain intracellular structures such as the chloroplast (or other plastid), endoplasmic reticulum, or Golgi apparatus, or to be secreted. For example, the gene can be engineered to contain a signal peptide to facilitate transfer of the peptide to the endoplasmic reticulum. By "signal sequence" is intended a sequence that is known or suspected to result in co-translational or post-translational peptide transport across the cell membrane. In eukaryotes, this typically involves secretion into the Golgi apparatus, with some resulting glycosylation. By "leader sequence" is intended any sequence that when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like. It may also be preferable to engineer the plant expression cassette to contain an intron, such that mRNA processing of the intron is required for expression.

By "3' untranslated region" is intended a nucleotide sequence located downstream of a coding sequence. Polyadenylation signal sequences and other sequences encoding regulatory signals capable of affecting the addition of polyadenylic acid tracts to the 3' end of the mRNA precursor are 3' untranslated regions. By "5' untranslated region" is intended a nucleotide sequence located upstream of a coding sequence.

Other upstream or downstream untranslated elements include enhancers. Enhancers are nucleotide sequences that act to increase the expression of a promoter region. Enhancers are well known in the art and include, but are not limited to, the SV40 enhancer region and the 35S enhancer element.

The termination region may be native with the transcriptional initiation region, may be native with the nitrogen-modulating sequence of the present invention, or may be derived from another source. Convenient termination regions are available from the Ti-plasmid of *A. tumefaciens*, such as the octopine synthase and nopaline synthase termination regions, or the potato proteinase inhibitor II sequence (PinII) as described in Liu et al. (2004) *Acta Biochim Biophys Sin* 36(8):553-558. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are known in the art for synthesizing host-preferred genes. See, for example, U.S. Pat. Nos. 6,320,100; 6,075,185; 5,380,831; and 5,436,391, U.S. Published Application Nos. 20040005600 and 20010003849, and Murray et al. (1989) *Nucleic Acids Res.* 17:477-498, herein incorporated by reference.

In one embodiment, the nucleic acids of interest are targeted to the chloroplast for expression. In this manner, where the nucleic acid of interest is not directly inserted into the chloroplast, the expression cassette will additionally contain a nucleic acid encoding a transit peptide to direct the gene product of interest to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Typically this "plant expression cassette" will be inserted into a "plant transformation vector." By "transformation vector" is intended a DNA molecule that is necessary for efficient transformation of a cell. Such a molecule may consist of one or more expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell.

This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors." Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "nucleotide sequence of interest" (a nucleotide sequence engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the gene of interest are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science,* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

Altered or Improved Variants Useful in the Constructs of the Invention

It is recognized that nucleotide and amino acid sequences useful in the present invention may be altered by various methods, and that these alterations may result in sequences encoding proteins with amino acid sequences different than that encoded by the nitrogen-modulating sequences disclosed herein.

Nucleotide sequences useful in the present invention include the sequences set forth in SEQ ID NO: 1 and 3, and combinations, variants, fragments, and complements thereof. As used herein, the term "nucleotide sequence" or "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecules can be single-stranded or double-stranded, but preferably are double-stranded DNA. By "complement" is intended a nucleotide sequence that is sufficiently complementary to a given nucleotide sequence such that it can hybridize to the given nucleotide sequence to thereby form a stable duplex. The corresponding amino acid sequences for the nitrogen-modulating proteins encoded by these nucleotide sequences are set forth in SEQ ID NO: 2 and 4, as well as combinations, variants and fragments thereof. The invention also encompasses the use of nucleic acid molecules comprising nucleotide sequences encoding partial-length nitrogen-modulating proteins, and complements thereof.

Nucleic acid molecules that are fragments of these nitrogen-modulating nucleotide sequences are also useful in the present invention. By "fragment" is intended a portion of a nucleotide sequence encoding a nitrogen-modulating protein. A fragment of a nucleotide sequence may encode a biologically active portion of a nitrogen-modulateing protein, or it may be a fragment that can be used as a hybridization probe or PCR primer using methods disclosed below. Nucleic acid molecules that are fragments of a nitrogen-modulating nucleotide sequence comprise at least about 15, 20, 50, 75, 100, 200, 300, 350, or at least about 400 contiguous nucleotides, or up to the number of nucleotides present in a full-length nitrogen-modulating nucleotide sequence disclosed herein depending upon the intended use. By "contiguous" nucleotides is intended nucleotide residues that are immediately adjacent to one another.

Polypeptides that are fragments of these nitrogen-modulating polypeptides are also useful in the present invention. By "fragment" is intended a portion of an amino acid sequence encoding a nitrogen-modulating protein as set forth SEQ ID NO: 2 and/or 4, and that retains nitrogen utilization efficiency. A biologically active portion of a nitrogen-modulating protein can be a polypeptide that is, for example, 10, 25, 50, 100, 125, 150, 175, 200, 250, 300, 350, 400 or more amino acids in length. Such biologically active portions can be prepared by recombinant techniques and evaluated for nitrogen utilization efficiency. As used here, a fragment comprises at least 8 contiguous amino acids of SEQ ID NO: 2 and/or 4. The invention encompasses other fragments, however, such as any fragment in the protein greater than about 10, 20, 30, 50, 100, 150, 200, 250, 300, 350, or 400 amino acids.

The invention also encompasses the use of variant nucleic acid molecules, or variant amino acid sequences, in the methods and compositions of the inventions. "Variants" of the nitrogen-modulating nucleotide sequences include those sequences that encode a nitrogen-modulating protein disclosed herein but that differ conservatively because of the degeneracy of the genetic code, as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the nitrogen-modulating proteins disclosed in the present invention as discussed below. Variant proteins useful in the present invention are biologically active, that is they retain the desired biological activity of the native protein, that is, nitrogen utilization efficiency and/or improved stress tolerance.

By "variants" is intended proteins or polypeptides having an amino acid sequence that is at least about 60%, 65%, about 70%, 75%, 80%, 85%, or 90%, 91%, 92%, 93%, 94%, 95%, 96%, 97%, 98% or 99% identical to the amino acid sequences of SEQ ID NO: 2 and/or 4. Variants also include polypeptides encoded by a nucleic acid molecule that hybridizes to a nucleic acid molecule of SEQ ID NO: 1 and/or 3, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retain nitrogen utilization efficiency and/or improved stress tolerance.

Preferred nitrogen-modulating proteins useful in the present invention are encoded by a nucleotide sequence sufficiently identical to a nucleotide sequence of SEQ ID NO: 1 and/or 3. The term "sufficiently identical" is intended an amino acid or nucleotide sequence that has at least about 60% or 65% sequence identity, about 70% or 75% sequence identity, about 80% or 85% sequence identity, or about 90%, 91%, 92%, 93%, 94%, 95%, 96%, 97%, 98% or 99% sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN® and BLASTX® programs of Altschul et al. (1990) *J. Mol. Biol.* 215:403. BLAST® nucleotide searches can be performed with the BLASTN® program, score=100, wordlength=12, to obtain nucleotide sequences homologous to nitrogen-modulating nucleic acid molecules of the invention. BLAST® protein searches can be performed with the BLASTX® program, score=50, wordlength=3, to obtain amino acid sequences homologous to nitrogen-modulating protein molecules of the invention. To obtain gapped alignments for comparison purposes, Gapped BLAST® can be utilized as described in Altschul et al. (1997) *Nucleic Acids Res.* 25:3389. Alternatively, PSI-Blast® can be used to perform an iterated search that detects distant relationships between molecules. See Altschul et al. (1997) supra. When utilizing BLAST®, Gapped BLAST®, and PSI-Blast® programs, the default parameters of the respective programs (e.g., BLASTX® and BLASTN®) can be used. Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX® module of the Vector NTI® Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN® program (version 2.0), which is part of the GCG sequence alignment software package (available from Accelrys, Inc., 9865 Scranton Rd., San Diego, Calif., USA). When utilizing the ALIGN® program for comparing amino acid sequences, a PAM120 weight residue table, a gap length penalty of 12, and a gap penalty of 4 can be used.

A preferred program is GAP version 10, which used the algorithm of Needleman and Wunsch (1970) *J. Mol. Biol.* 48:443-453. GAP Version 10 may be used with the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 Scoring Matrix. Equivalent programs may also be used. By "equivalent program" is intended any sequence comparison program that, for any two sequences in question, generates an alignment having identical nucleotide or amino acid residue matches and an identical percent sequence identity when compared to the corresponding alignment generated by GAP Version 10.

The skilled artisan will further appreciate that changes can be introduced by mutation into the nucleotide sequences of the invention thereby leading to changes in the amino acid sequence of the encoded nitrogen-modulating protein, without altering the biological activity of the protein. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more predicted, preferably nonessential amino acid residues. A "nonessential" amino acid residue is a residue that can be altered from the wild-type sequence of a nitrogen-modulating protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Amino acid substitutions may be made in nonconserved regions that retain function. In general, such substitutions would not be made for conserved amino acid residues, or for amino acid residues residing within a conserved motif, where such residues are essential for protein activity. However, one of skill in the art would understand that functional variants may have minor conserved or nonconserved alterations in the conserved residues. Examples of residues that are conserved and that may be essential for protein activity include, for example, residues that are identical between all proteins contained in an alignment of similar or related sequences known to be involved in nitrogen assimilation. Examples of residues that are conserved but that may allow conservative amino acid substitutions and still retain activity include, for example, residues that have only conservative substitutions between all proteins contained in an alignment of similar or related sequences known to be involved in nitrogen assimilation.

Alternatively, variant nucleotide sequences can be made by introducing mutations randomly along all or part of the coding sequence, such as by saturation mutagenesis, and the resultant mutants can be screened for ability to confer nitrogen utilization efficiency to identify mutants that retain activity. Following mutagenesis, the encoded protein can be expressed recombinantly, and the activity of the protein can be determined using standard assay techniques.

Using methods such as PCR, hybridization, and the like, corresponding nitrogen-modulating sequences can be identified, such sequences having substantial identity to the sequences of the invention. See, for example, Sambrook J., and Russell, D. W. (2001) *Molecular Cloning: A Laboratory Manual*. (Cold Spring Harbor Laboratory Press, Cold Spring Harbor, N.Y.) and Innis, et al. (1990) *PCR Protocols: A Guide to Methods and Applications* (Academic Press, NY). In a hybridization method, all or part of the nitrogen-modulating nucleotide sequence can be used to screen cDNA or genomic libraries. Methods for construction of such cDNA and genomic libraries are generally known in the art and are disclosed in Sambrook and Russell, 2001, supra.

Variants and fragments of the nucleotide or amino acid sequences of the present invention generally will encode protein fragments that retain the biological activity of the full-length nitrogen-modulating protein; i.e., retain nitrogen utilization efficiency. By "retains nitrogen utilization efficiency" is intended that the variant or fragment will have at least about 30%, at least about 50%, at least about 70%, or at least about 80% of the nitrogen utilization efficiency and/or stress tolerance of the full-length nitrogen-modulating protein disclosed herein as SEQ ID NO: 2 and/or 4, or the full-length nitrogen-modulating nucleotide sequence disclosed herein as SEQ ID NO: 1 and/or 3. Methods for monitoring nitrogen utilization efficiency include detecting a change in any of the main nitrogen metabolic pool sizes in the assimilation pathways (for example, a measurable change in nitrate, nitrite, ammonia, glutamic acid, aspartic acid, glutamine, asparagine, lysine, leucine, threonine, methionine, glycine, tryptophan, tyrosine, total protein content of a plant part, total nitrogen content of a plant part, and/or chlorophyll content) or detecting the ability of a plant to provide the same or elevated yield at lower nitrogen fertilization levels, or the ability of a plant to provide elevated yields at the same nitrogen fertilization levels when compared to a plant that does not contain or express a nitrogen-modulating sequence of the invention. The designation of "same" or "lower" nitrogen fertilization levels refers to the level of nitrogen generally applied to a plant not expressing a nitrogen-modulating sequence of the invention. Sufficient nitrogen levels are known in the art for the majority, if not all, plant varieties of interest. Additional guidance may be found in, for example, Hewitt (1966) *Sand and Water Culture Methods Used in the Study of Plant Nutrition,* 2nd ed., Farnham Royal (Bucks), Commonwealth Agricultural Bureaux; and, Hewitt (1975) *Plant Mineral Nutrition*, London, English University Press.

The polypeptide sequences useful in the present invention may be altered in various ways including amino acid substitutions, deletions, truncations, and insertions. Methods for such manipulations are generally known in the art. For example, amino acid sequence variants of the nitrogen-modulating proteins disclosed herein can be prepared by mutations in the nucleotide sequences. This may also be accomplished by one of several forms of mutagenesis and/or in directed evolution. In some aspects, the changes encoded in the amino acid sequence will not substantially affect function of the protein. Such variants will possess the desired nitrogen utilization efficiency. However, it is understood that the ability of the nitrogen-modulating sequences of the invention to alter or improve nitrogen utilization may be further improved by one use of such techniques upon the compositions of this invention. For example, one may express the nucleotide sequences disclosed herein in host cells that exhibit high rates of base misincorporation during DNA replication, such as XL-1 Red (Stratagene, La Jolla, Calif.). After propagation in such strains, one can isolate the DNA (for example by preparing plasmid DNA, or by amplifying by PCR and cloning the resulting PCR fragment into a vector), transform it into plants as described elsewhere herein, and measure nitrogen utilization efficiency.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest, (2) introduce a binding domain, enzymatic activity, or epitope to facilitate either protein purification, protein detection, or other experimental uses known in the art, or, (3) target secretion or translation of a protein to a subcellular organelle, such as the periplasmic space of gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different nitrogen-modulating protein coding regions can be used to create a new nitrogen-modulating protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the nitrogen-modulating sequence useful in the present invention and other known nitrogen-modulating sequences to obtain a new sequence coding for a protein with an improved property of interest, such as improved nitrogen utilization. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Plant Transformation

Methods of the invention involve introducing one or more nitrogen-modulating nucleotide sequences into a plant. In some embodiments, only one of the nitrogen-modulating sequences disclosed herein is introduced into the plant. In other embodiments, at least 2, at least 3, at least 4, or more of the sequences are introduced. Where multiple sequences are introduced, each of the nucleotide sequences is non-identical. Two nucleotide sequences are considered non-identical if they differ in at least one nucleotide position. Thus, non-identical nucleotide sequences include two or more different nucleotide sequences that each encodes the same amino acid sequence (e.g., one or more has been optimized for expression in the plant), as well as two or more different nucleotide sequences that encode at least two different amino acid sequences.

By "introducing" it is intended to present to the plant one or more constructs comprising the one or more nitrogen-modulating sequences in such a manner that the construct(s) gain(s) access to the interior of a cell of the plant. The methods of the invention do not require that a particular method for introducing a nucleotide construct to a plant is used, only that the nucleotide construct(s) gain(s) access to the interior of at least one cell of the plant. Methods for introducing nucleotide constructs into plants are known in the art including, but not limited to, stable transformation methods, transient transformation methods, and virus-mediated methods.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent (i.e., antibiotics, such as spectinomycin and kanamycin). The shoots are then transferred to a selective rooting medium for recovering rooted shoot or plantlet. The transgenic plantlet then grow into mature plant and produce fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells, both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants. Molecular and biochemical methods can then be used to confirm the presence of the integrated heterologous gene of interest in the genome of transgenic plant.

Generation of transgenic plants may be performed by one of several methods, including but not limited to introduction of heterologous DNA by *Agrobacterium* into plant cells (*Agrobacterium*-mediated transformation), bombardment of plant cells with heterologous foreign DNA adhered to particles, and various other non-particle direct-mediated methods (e.g. Hiei et al. (1994) *The Plant Journal* 6:271-282; Ishida et al. (1996) *Nature Biotechnology* 14:745-750; Ayres and Park (1994) *Critical Reviews in Plant Science* 13:219-239; Bommineni and Jauhar (1997) *Maydica* 42:107-120) to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

Transformation of bacterial cells is accomplished by one of several techniques known in the art, including but not limited to electroporation or chemical transformation (see, for example, Ausubel, ed. (1994) Current Protocols in Molecular Biology, John Wiley and Sons, Inc., Indianapolis, Ind.). Markers conferring resistance to toxic substances are useful in identifying transformed cells (having taken up and expressed the test DNA) from non-transformed cells (those not containing or not expressing the test DNA).

In one aspect of the invention, the nucleotide sequences of the invention are useful as markers to assess transformation of bacterial or plant cells. In this manner, transformation is assessed by monitoring nitrogen utilization efficiency as described above.

Transformation of plant cells can be accomplished in similar fashion. By "plant" is intended whole plants, or component parts including plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen). "Transgenic plants" or "transformed plants" or "stably transformed" plants or cells or tissues refer to plants that have incorporated or integrated exogenous nucleic acid sequences or DNA fragments into the plant cell. By "stable transformation" is intended that the nucleotide construct introduced into a plant integrates into the genome of the plant and is capable of being inherited by progeny thereof.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Methods to Increase Plant Yield by Modulating Nitrogen Utilization

Methods for increasing plant yield are provided. The methods comprise introducing into a plant or plant cell a nitrogen-modulating nucleotide sequence disclosed herein such that an increase in nitrogen utilization efficiency corresponds to an increase in plant yield. As defined herein, the "yield" of the plant refers to the quality and/or quantity of biomass, and/or harvestable yield, produced by the plant. By "biomass" is intended any measured plant product (e.g., any component part of a plant, such as seed, stalk, root, grain, leaf, etc.). An increase in biomass production is any improvement in the yield of the measured plant product. An increase in harvestable yield is a higher weight of a plant component that is easily collected using known harvest methods, or an increase in the compositional amount of a compound of interest in the harvested part: a nonlimiting example, being the amount of an amino acid, such as lysine, that is harvested per unit land area. Increasing plant yield or harvestable yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in plant yield compared to the yield of a plant into which a nucleotide sequence that modulates use of nitrogen of the invention has not been introduced.

Plants

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, grasses (such as turf grasses, forage grasses, or pasture grasses), ornamentals, trees (such as fruit trees, nut trees, pulp trees, oil palms) and conifers.

Vegetables include, but are not limited to, onions, tomatoes, lettuce, green beans, lima beans, peas, and members of the genus *Curcumis* such as cucumber, cantaloupe, and muskmelon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

This invention is particularly suitable for any member of the monocot plant family including, but not limited to, maize, rice, barley, oats, wheat, sorghum, rye, sugarcane, pineapple, yams, onion, banana, coconut, and dates.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated nucleotide sequences at the earlier stage before transplanting into the soil (Sambrook and Russell (2001) *Molecular Cloning: A Laboratory Manual*, Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled $^{32}$P target DNA fragments to confirm the integration of the introduced gene in the plant genome according to standard techniques (Sambrook and Russell, 2001, supra).

In Northern analysis, RNA is isolated from specific tissues of transformant, fractionated in a formaldehyde agarose gel, blotted onto a nylon filter according to standard procedures that are routinely used in the art (Sambrook and Russell, 2001, supra). Expression of RNA encoded by the nucleotide sequence of the invention is then tested by hybridizing the filter to a radioactive probe derived from a polynucleotide of the invention, by methods known in the art (Sambrook and Russell, 2001, supra)

Western blot and biochemical assays and the like may be carried out on the transgenic plants to determine the presence of protein encoded by the nitrogen-modulating gene by standard procedures (Sambrook and Russell, 2001, supra) using antibodies that bind to one or more epitopes present on the nitrogen-modulating protein. For example, the polyclonal antibodies generated by the methods of the present invention can be used to detect the presence of a nitrogen-modulating protein.

Antibodies

Antibodies to the polypeptides useful in the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

EXPERIMENTAL

I. icdh Gene

Materials and Methods

Using genomic tools, multiple searches were made among the plant and bacterial icdh genes in Genbank. The target focus was on cytosolic, monomeric, NADP+-dependent versions, and with a particular "AT" pattern in the polyA signals that would not be inhibitory to expression in plants. This work eventually led to a sequence from an *Azotobacter* species that had a fit with the criteria. The sequence of the selected bacterial isocitrate dehydrogenase gene (icdh) was codon optimized for expression in maize. A synthetic gene encoding an ICDH enzyme was generated (SEQ ID NO: 1):

ATGAGCACCCCCAAGATCATCTACACCTTGACAGATGAGGCGCCGGCGCT

GGCCACCTACAGCTTGCTGCCCATCATCAAGGCTTTCACTGGAAGCTCAG

GCATTGCTGTGGAAACAAGGGACATCTCCCTTGCTGGAAGGCTGATCGCC

ACCTTCCCAGAATATTTGACAGACACCCAGAAGATCTCTGATGATCTTGC

TGAGCTGGGGAAGCTGGCCACCACGCCAGATGCCAACATCATCAAGCTGC

CAAACATCTCTGCTTCAGTTCCTCAGCTGAAGGCCGCCATCAAGGAACTC

CAGCAGCAAGGCTACAAGCTGCCAGATTATCCAGAAGAACCAAAAACAGA

CACAGAGAAGGATGTCAAGGCAAGATATGACAAGATCAAGGGCAGCGCCG

TCAACCCCGTGCTGAGAGAAGGAAATTCAGACCGCCGCGCGCCGCTCTCC

GTCAAGAACTATGCAAGGAAGCATCCTCACAAGATGGGCGCCTGGAGCGC

CGACAGCAAGAGCCATGTTGCTCACATGGACAATGGAGATTTCTATGGAT

CAGAGAAGGCGGCGCTGATTGGTGCTCCTGGAAGCGTCAAGATTGAGCTG

ATCGCCAAGGATGGAAGCAGCACCGTGCTGAAGGCCAAGACATCAGTTCA

AGCTGGAGAGATCATCGACAGCTCCGTGATGAGCAAGAATGCTCTGAGGA

ACTTCATTGCTGCCGAGATTGAAGATGCCAAGAAGCAAGGAGTGCTGCTC

TCCGTCCACCTCAAGGCCACCATGATGAAGGTTTCAGATCCCATCATGTT

TGGCCAGATTGTTTCAGAGTTCTACAAGGATGCTCTCACCAAGCATGCTG

AGGTGCTGAAGCAGATTGGATTTGATGTCAACAATGGCATTGGAGATCTC

TATGCAAGGATCAAGACCCTACCAGAAGCAAAGCAGAAGGAGATTGAAGC

TGACATCCAAGCTGTTTATGCTCAAAGGCCGCAGCTGGCAATGGTGAACA

GCGACAAGGGCATCACCAACCTCCATGTTCCTTCTGATGTCATCGTCGAC

GCCTCCATGCCGGCCATGATCAGAGATTCAGGGAAGATGTGGGGGCCAGA

TGGCAAGCTGCATGACACCAAGGCCGTCATCCCAGATCGCTGCTATGCTG

GCGTCTACCAGGTGGTGATTGAAGATTGCAAGCAGCATGGCGCCTTCGAC

CCAACAACAATGGGCTCAGTTCCAAATGTTGGGCTGATGGCGCAGAAGGC

AGAAGAATATGGAAGCCATGACAAGACCTTTCAGATCCCTGCTGATGGCG

TCGTCCGCGTCACTGATGAAAGCGGCAAGCTGCTGCTGGAGCAATCAGTG

GAAGCTGGAGACATCTGGAGGATGTGCCAAGCAAAGGATGCTCCCATCCA

AGATTGGGTGAAGCTCGCCGTCAACAGGGCGCGCGCCACCAACACGCCGG

CGGTGTTCTGGCTGGACCCAGCAAGGGCTCATGATGCTCAGGTGATCGCC

AAGGTGGAGAGATATCTAAAGGATTATGACACCTCCGGCCTGGACATCAG

GATCTTGTCGCCGGTGGAAGCAACAAGGTTCTCCTTGGCAAGGATCAGAG

AAGGAAAGGACACCATCTCAGTGACAGGAAATGTGCTGAGGGACTACCTC

ACCGACCTCTTCCCCATCATGGAGCTGGGCACCTCCGCCAAGATGCTCTC

CATTGTTCCTCTGATGAGCGGCGGCGGCCTCTTTGAAACTGGAGCTGGAG

GATCAGCGCCCAAGCATGTTCAGCAGTTCCTGGAAGAAGGCTACCTCAGA

TGGGACAGCCTTGGAGAGTTCCTGGCGCTCGCCGCCTCCTTGGAGCATCT

TGGAAATGCCTACAAGAACCCAAAGGCGCTGGTGCTGGCCTCCACCCTAG

ATCAAGCTACTGGCAAGATCCTGGACAACAACAAGAGCCCAGCAAGGAAG

GTTGGTGAGATCGACAACAGAGGAAGCCACTTCTACCTGGCGCTCTACTG

GGCTCAAGCTCTTGCTGCTCAAACAGAGGACAAGGAGCTACAAGCTCAGT

TCACCGGCATTGCCAAGGCGCTGACAGACAATGAAACAAAAATTGTTGGA

GAGCTGGCTGCTGCTCAAGGAAAGCCGGTGGACATTGCTGGCTACTACCA

TCCAAACACCGACCTCACCAGCAAGGCCATCAGGCCATCTGCCACCTTCA

ATGCTGCTCTGGCGCCGCTGGCATAGTAAGG

The icdh DNA sequence shown above encodes the following ICDH protein sequence (SEQ ID NO:2) (741 amino acids):

```
mstpkiiytl tdeapalaty sllpiikaft gssgiavetr
dislagrlia tfpeyltdtq kisddlaelg klattpdani
iklpnisasv pqlkaaikel qqqgyklpdy peepktdtek
dvkarydkik gsavnpvlre gnsdrrapls vknyarkhph
kmgawsadsk shvahmdngd fygsekaali gapgsvkiel
iakdgsstvl kaktsvqage iidssvmskn alrnfiaaei
edakkqgvll svhlkatmmk vsdpimfgqi vsefykdalt
khaevlkqig fdvnngigdl yariktlpea kqkeieadiq
avyaqrpqla mvnsdkgitn lhvpsdvivd asmpamirds
gkmwgpdgkl hdtkavipdr cyagvyqvvi edckqhgafd
pttmgsvpnv glmaqkaeey gshdktfqip adgvvrvtde
sgkllleqsv eagdiwrmcq akdapiqdwv klavnrarat
ntpavfwldp arandaqvia kverylkdyd tsgldirils
pveatrfsla riregkdtis vtgnvirdyl tdlfpimelg
tsakmlsivp lmsggglfet gaggsapkhv qqfleegylr
wdslgeflal aaslehlgna yknpkalvla stldqatgki
ldnnkspark vgeidnrgsh fylalywaqa laaqtedkel
qaqftgiaka ltdnetkivg elaaaqgkpv diagyyhpnt
dltskairps atfnaalapl a
```

Vector Construction for Overexpression of ICDH

The open reading frame described in the previous section was introduced into a vector for plant expression. The vector also contains a gene encoding a glyphosate tolerant EPSPS enzyme (GRG23ace5) that was used as the selectable marker during maize transformation. Expression of each these genes was controlled by the ScUbi4 promoter to produce robust expression in maize. A vector map of this vector, denominated pMDO8901, is shown in FIG. 1.

Plant Transformation

The pMDO8901 vector was used to carry out Agrobacterium-mediated transformation of maize. Following vector construction and transformation of Agrobacterium, the vectors were confirmed by Southern blot by methods known in the art. Positive Agrobacterium strains that passed these tests were then grown on a solid medium to produce cell counts for large-scale transformation experiments.

The vector pMDO8901 was introduced into an Agrobacterium tumefaciens strain by electroporation. The formation of the recombinant vector, pMDO8901, was confirmed by Southern blot hybridization of this Agrobacterium strain. The selection agent for these experiments was glyphosate The Agrobacterium strain harboring the cointegrate can be used to transform plants, for example, by the PureIntro method (Japan Tobacco, Inc.).

Western Blot Analysis

Expression of icdh in these plants was examined by generating antibodies that bind specifically to the ICDH protein. Briefly, the icdh gene was subcloned into the vector pRSF1b (Novagen) to allow overexpression of the ICDH protein in E. coli following IPTG induction. The vector also introduces a 6×His tag at the N-terminus of the protein. Following protein overexpression, the ICDH protein was purified by cobalt column chromatography and the identity of the purified protein was confirmed by N-terminal sequencing. The purified protein was then used to immunize rabbits, with serum collection beginning 42 days after immunization.

Next, the ICDH antiserum was used to assess protein expression in the transgenic maize plants by Western blot analysis. Leaf samples were taken from individual plants following 4 weeks of growth in the greenhouse, and protein extracts were prepared by grinding the plant material in water. Protein concentration in each extract was determined by Bradford assay, and 25 ug of each extract was separated on polyacrylamide gels with a 4-12% gradient. The separated proteins were transferred to nitrocellulose and then probed with the rabbit antiserum at a 1:5000 dilution. Following wash steps, the nitrocellulose was contacted with goat anti-rabbit conjugated with horseradish peroxidase (1:10,000 dilution), and antibody complexes were visualized using ECL detection reagents (GE Healthcare). At the T0 stage most icdh events were found to be expressing ICDH. Two events had particularly good expression levels and were promoted to the T1 stage.

Maize Nitrogen Analysis

A series of assays that quantify nitrogen intermediates in plants have been developed. These nitrogen assay methods are described in a previous patent filing (WO 2008/051608 "Plants with improved nitrogen utilization and stress tolerance"). These assays were utilized here to analyze a total of 10 transgenic plants containing the icdh gene. Each of the plants was sampled (leaf) following 4 weeks of growth in soil in a greenhouse. These leaf samples were processed to determine their nitrate, asparagine, glutamine, aspartic acid, glutamic acid, ammonium, total amino acid, chlorophyll, and total protein levels. Included alongside in the analysis were plants that were transformed with a construct containing only the GRG23ace5 selectable marker (no icdh nor nagk). These plants were likewise sampled at 4 weeks and are referred to as "non-GOI" plants. The results of the nitrogen assays carried out on both types of plants are shown below in Table 1.

TABLE 1

Nitrogen levels, ICDH vs. non-GOI maize events, 4 weeks after transfer to soil

| Plant # | GOI | Aspartic Acid (µg/g) | Glutamic Acid (µg/g) | Asparagine (µg/g) | Glutamine (µg/g) | Total Chlorophyll (a + b) (mg/g) | Ammonium (µg/g) | Total Amino Acids (mg/g) | Total Protein (mg/g) |
|---|---|---|---|---|---|---|---|---|---|
| 15091 | ICDH | 177.3 | 1240.2 | 1692.0 | 5175.0 | 0.086 | 755.795 | 285.830 | 16.990 |
| 15092 | ICDH | 451.7 | 1161.9 | 1898.3 | 2055.2 | 0.007 | 533.265 | 234.620 | 25.471 |
| 15093 | ICDH | 82.9 | 962.6 | 450.0 | 1344.0 | 0.061 | 502.607 | 157.230 | 24.621 |
| 15094 | ICDH | 201.3 | 1417.4 | 148.9 | 2144.1 | 0.074 | 670.780 | 166.334 | 19.411 |
| 15095 | ICDH | 174.9 | 1176.2 | 1403.1 | 3009.6 | 0.066 | 714.197 | 196.974 | 22.753 |
| 15096 | ICDH | 51.2 | 1435.5 | 2006.0 | 2630.9 | 0.052 | 626.751 | 302.167 | 20.094 |

TABLE 1-continued

Nitrogen levels, ICDH vs. non-GOI maize events, 4 weeks after transfer to soil

| Plant # | GOI | Aspartic Acid (µg/g) | Glutamic Acid (µg/g) | Asparagine (µg/g) | Glutamine (µg/g) | Total Chlorophyll (a + b) (mg/g) | Ammonium (µg/g) | Total Amino Acids (mg/g) | Total Protein (mg/g) |
|---|---|---|---|---|---|---|---|---|---|
| 15097 | ICDH | 213.6 | 1213.7 | 1364.2 | 2357.3 | 0.054 | 634.482 | 207.681 | 24.317 |
| 15098 | ICDH | 256.4 | 1762.7 | 3595.3 | 5148.4 | 0.357 | 1822.651 | 448.316 | 42.052 |
| 15099 | ICDH | 82.4 | 848.0 | 1946.7 | 2503.9 | 0.064 | 590.783 | 201.124 | 19.159 |
| 15100 | ICDH | 208.4 | 1562.0 | 2226.4 | 4765.9 | 0.061 | 1140.701 | 303.099 | 19.038 |
| 15101 | ICDH | 167.6 | 914.3 | 1184.2 | 2873.7 | 0.049 | 542.457 | 267.801 | 18.433 |
| 15122 | ICDH | 269.2 | 1081.6 | 1424.1 | 6786.6 | 0.061 | 574.964 | 265.796 | 35.271 |
| 15123 | ICDH | 322.1 | 1713.5 | 1625.9 | 7988.8 | 0.062 | 24.671 | 375.517 | 23.669 |
| 15124 | ICDH | 296.5 | 1262.3 | 1138.7 | 6023.9 | 0.077 | 367.674 | 237.945 | 29.045 |
| 15125 | ICDH | 387.2 | 2006.6 | 1652.1 | 7789.2 | 0.079 | 926.448 | 289.497 | 30.555 |
| IC 1 Control | non-GOI | 537.8 | 596.3 | 2335.0 | 3516.7 | 0.154 | 984.302 | 362.225 | 28.635 |
| IC 2 Control | non-GOI | 101.6 | 473.7 | 1490.3 | 2485.0 | 0.157 | 505.712 | 264.265 | 34.564 |
| IC 3 Control | non-GOI | 153.6 | 914.9 | 1799.3 | 2191.5 | 0.066 | 534.599 | 297.756 | 34.019 |
| IC 4 Control | non-GOI | 59.7 | 526.2 | 313.0 | 659.3 | 0.082 | 347.337 | 183.701 | 24.077 |
| Avg | | 213.2 | 627.8 | 1484.4 | 2213.1 | 0.114 | 984.3 | 277.0 | 30.3 |
| Std Dev | | 219.8 | 197.9 | 855.4 | 1181.5 | 0.048 | 273.6 | 74.3 | 5.0 |

These data demonstrate that the synthetic gene we designed encodes a functional ICDH enzyme.

Maize Plants Containing Icdh Gene Showed Differences Over Controls

Events 15122 and 15125 were selected and progressed onto the T1 stage. The T1 plants were sampled and evaluated as described previously. The results are set out in Tables 2-4.

TABLE 2

T0 Event Promoted to T1 Testing Due to Elevated Glutamine

| 15122 Plant # | GOI | Aspartic Acid (µg/g) | Glutamic Acid (µg/g) | Asparagine (µg/g) | Glutamine (µg/g) | Total Chlorophyll (a + b) (mg/g) | Ammonium (µg/g) | Total Amino Acids (mg/g) | Total Protein (mg/g) |
|---|---|---|---|---|---|---|---|---|---|
| 2 | ICDH | 331 | 2537 | 575 | 2551 | 0.197 | 566 | 229 | 18.6 |
| 3 | ICDH | 456 | 2299 | 647 | 2105 | 0.144 | 477 | 254 | 18.1 |
| 5 | ICDH | 563 | 2880 | 220 | 2106 | 0.450 | 294 | 170 | 12.9 |
| 7 | ICDH | 1151 | 2350 | 671 | 2628 | 0.243 | 351 | 217 | 22.5 |
| 8 | ICDH | 664 | 2707 | 466 | 3826 | 0.115 | 413 | 202 | 14.0 |
| 9 | ICDH | 446 | 3155 | 89 | 1156 | 0.148 | 406 | 163 | 27.9 |
| Avg | | 602 | 2655 | 445 | 2396 | 0.216 | 418 | 206 | 19.0 |
| Std Dev | | 292 | 328 | 240 | 875 | 0.123 | 95 | 35 | 5.6 |

TABLE 3

T0 Event Promoted to T1 Testing Due to Elevated Aspartic Acid, Glutamic Acid and Glutamine

| 15122 Plant # | GOI | Aspartic Acid (µg/g) | Glutamic Acid (µg/g) | Asparagine (µg/g) | Glutamine (µg/g) | Total Chlorophyll (a + b) (mg/g) | Ammonium (µg/g) | Total Amino Acids (mg/g) | Total Protein (mg/g) |
|---|---|---|---|---|---|---|---|---|---|
| 1 | ICDH | 478 | 2929 | 140 | 3961 | 0.166 | 609 | 204 | 21.6 |
| 2 | ICDH | 827 | 1912 | 855 | 4177 | 0.207 | 391 | 256 | 19.3 |
| 3 | ICDH | 838 | 2406 | 416 | 4364 | 0.157 | 613 | 251 | 14.2 |
| 4 | ICDH | 865 | 24410 | 606 | 6268 | 0.284 | 376 | 192 | 28.2 |
| 5 | ICDH | 391 | 2564 | 167 | 2447 | 0.184 | 535 | 221 | 17.3 |
| 10 | ICDH | 328 | 3010 | 376 | 2128 | 0.209 | 417 | 345 | 14.0 |
| Avg | | 621 | 6205 | 427 | 3891 | 0.201 | 490 | 245 | 19.1 |
| Std Dev | | 248 | 8927 | 271 | 1494 | 0.046 | 109 | 55 | 5.3 |

TABLE 4

| | | | | | | Total | | Total | |
| Control Plant # | GOI | Aspartic Acid (µg/g) | Glutamic Acid (µg/g) | Asparagine (µg/g) | Glutamine (µg/g) | Chlorophyll (a + b) (mg/g) | Ammonium (µg/g) | Amino Acids (mg/g) | Total Protein (mg/g) |
| --- | --- | --- | --- | --- | --- | --- | --- | --- | --- |
| 1 | | 253 | 2351 | 1759 | 2412 | 0.298 | 567 | 235 | 22.0 |
| 2 | | 739 | 2154 | 3488 | 3989 | 0.089 | 452 | 226 | 17.4 |
| 3 | | 297 | 1767 | 373 | 2532 | 0.107 | 408 | 197 | 21.2 |
| 4 | | 905 | 2233 | 941 | 3237 | 0.145 | 314 | 190 | 17.2 |
| 5 | | 394 | 3037 | 3346 | 5262 | 0.155 | 504 | 252 | 19.5 |
| 6 | | 789 | 2535 | 4166 | 9084 | 0.133 | 459 | 295 | 28.9 |
| Avg | | 563 | 2346 | 2346 | 4419 | 0.154 | 451 | 232 | 21.0 |
| Std Dev | | 281 | 424 | 1538 | 2516 | 0.074 | 86 | 38 | 4.3 |

Controls

The data for T1 plants indicated lower asparagine levels for the transgenic events (both the average and for most plants). Individual plants had results that differed from the control; for example, event 15122 plant #5, had higher glutamic acid and higher chlorophyll but lower amino acids and lower protein levels compared to the controls.

In Event 15125, plant #4 had much a higher level of glutamic acid. The recorded number was so high as to appear that it might be an outlier or a sampling error. However, the same plant had higher chlorophyll and higher protein levels compared to the control (the chlorophyll and protein measurements are taken from a separate sample than the glutamine), therefore all the elevated levels could not have been due to the same experimental error, even if one assumed there was an error for glutamine.

Overall the data indicates some potential effects on the measured pool sizes (e.g. lower asparagine) and others for individual plants (e.g. chlorophyll). Lower asparagine could be due to more N incorporation into other pools resulting in less N for internal transport (via the transport amino acid, asparagine).

II. icdh Gene+nagk Gene

Vector Construction for Overexpression of Bacterial icdh+nagk

Figure 2:
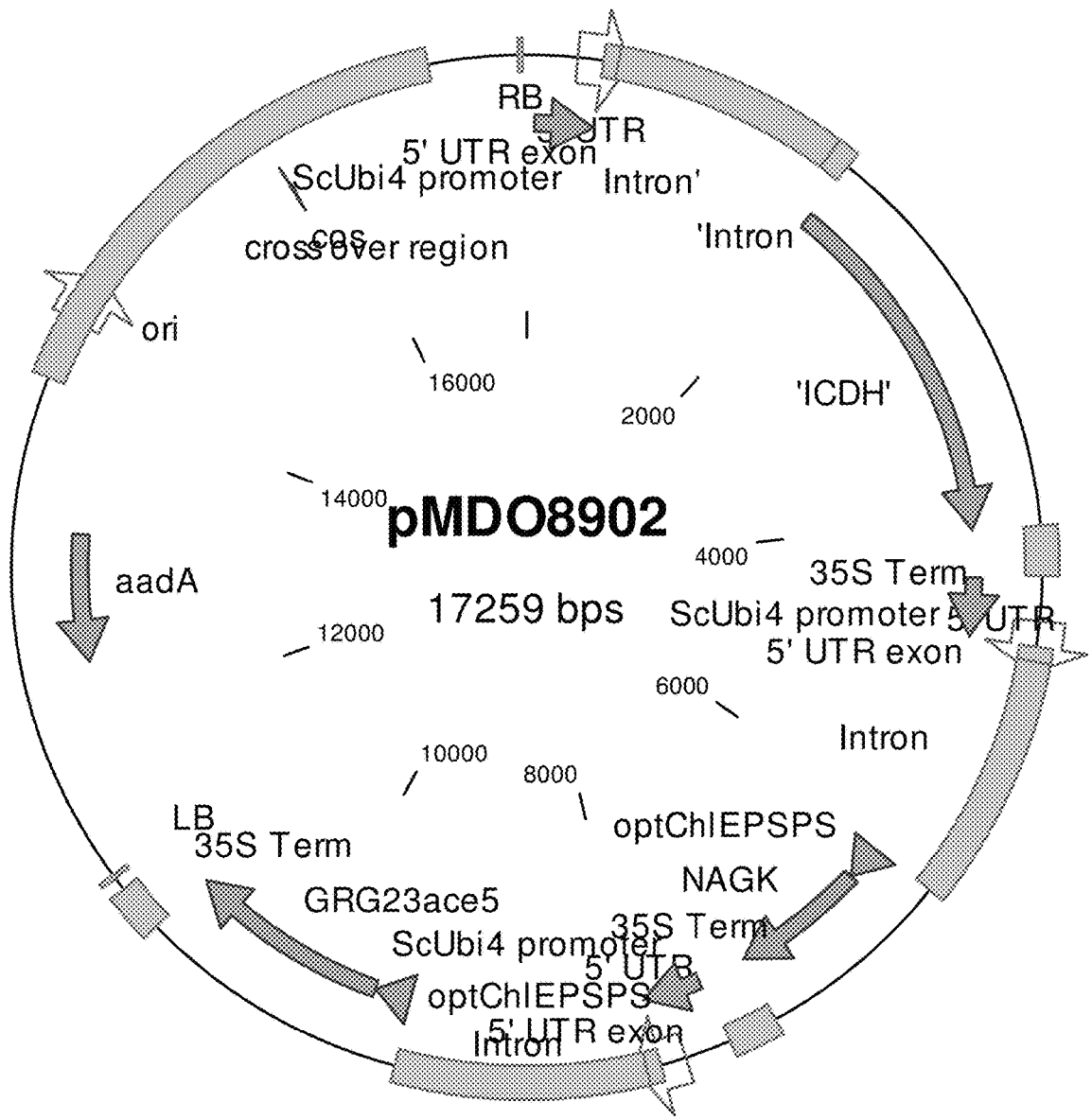
FIG. 2 is a vector map for the plasmid pMDO8902, wherein the main elements in the plasmid (clockwise from top) are: Right Border, ScUbi4 promoter, 5' UTR exon, intron, icdh gene, 35S terminator, ScUbi4 promoter, 5' UTR exon, intron, chloroplast transit peptide from EPSPS, nagk gene, 35S terminator, ScUbi4 promoter, 5' UTR exon, intron, glyphosate tolerance SM, 35S terminator, Left Border.

The ICDH vector pMDO8901 was further modified to add a gene encoding an arginine-insensitive N-acetylglutamate kinase (NAGK) protein. This new vector (pMDO8902; FIG. 2) is designed to introduce overexpression of both ICDH and NAGK proteins to further improve nitrogen utilization in plants.

The DNA sequence encoding NAGK, SEQ ID NO: 3 set out below, includes a chloroplast transit peptide (CTP) obtained from the 5' end of the enolpyruvyl shikimate phosphate synthase (EPSPS) gene from the algae *Chlamydomonas reinhardtii*. The sequence of the CTP is distinguished from the nagk gene in that the nagk gene is shown in boldface type:

SEQ ID NO: 3
ATGCAGCTGCTCAACCAGCGGCAGGCGCTGCGGCTGGGAAGAAGCTCCGC

CAGCAAGAACCAGCAGGTGGCGCCGCTGGCATCAAGGCCGGCAAGCAGCC

TCTCCGTCTCCGCCTCCTCCGTGGCGCCGGCGCCGGCCTGCTCGGCGCCG

GCCGGCGCCGGCCGCCGCGCCGTGGTGGTGCGCGCCTCCGCCACCAAGGA

GAAGGIGGAGGAGCTCACCATCCAGATGCTGCATGAGGTGATGGTGATCA

AGTGCGGCGGCAGCATGCTGGAGCAGCTGCCGGAGAGCTTCTACAACAAG

CTGGCGACGCTGCAAGCAGAAGGAAGAAGCATCGTCATTGTTCATGGAGG

AGGGCCGGCCATCAACCAGATGCTGGAGCAGCTGAAGATTGAGCCAACCT

TCTCAAATGGGCTGAGGGTGACAGATGAGCCAACAATGCAAGCTGTGGAG

ATGGTGCTCTCAGGGCCCATCAACAAGCTGGTGGTGAGGAAGCTGCTGCA

CGCCGGCGGCAAGGCATGGGGCCTCAGCGGCGTGGATGGAAGCCTGCTGC

AAGCTGTTGAGAAGACTCAAGGCCTCGGCCTGGTGGGCAGCATCACCGTG

GTGGATCAAGCGCCGCTCCAGCTGCTGCTGAGCAATGGCTACATCCCGGT

GGTGTCTCCCATCGCCGTCTCAGAAGATGGAAGAACAAGATACAACTGCA

ACGCCGACACCGTCGCCGGCGCCATTGCTTCAGCTCTCGGCGCCAAGCAG

CTGCTGATGCTCACTGATGTTCCTGGCATCTGGGCAGAAAATGAGCTGGG

AGAGAAGCAGCTGCTGCCGACGGTGACAACAGAAGATATTCAGCTGATGA

TGAAGAACCAGATCATCACCGGCGGCATGATCCCCAAGGTGCAAGCGGCG

CTGGATGCTCTAGCTCAAGGAGTTCAAGAAGTGGTGATCTGCAAAGGAGA

AGCTGAGACGCTGGACGGCGTGGTGAAGGGCATGGCCGTCGGCACCTCCA

TCTCCGCCGAGATGAGCAGAGGACAAGATTCTCAAGCCTTCATCAGCAAC

AAGGTGTGAGG

This amino acid sequence of NAGK (after removal of the CTP), SEQ ID NO: 4, is shown here (277 amino acids):

SEQ ID NO: 4:
MLHEVMVIKC GGSMLEQLPE SFYNKLATLQ AEGRSIVIVH

GGGPAINQML EQLKIEPTFS NGLRVTDEPT MQAVEMVLSG

PINKLVVRKL LHAGGKAWGL SGVDGSLLQA VEKTQGLGLV

GSITVVDQAP LQLLLSNGYI PVVSPIAVSE DGRTRYNCNA

DTVAGAIASA LGAKQLLMLT DVPGIWAENE LGEKQLLPTV

TTEDIQLMMK NQIITGGMIP KVQAALDALA QGVQEVVICK

GEAETLDGVV KGMAVGTSIS AEMSRGQDSQ AFISNKV

Maize Transformation with Vector pMDO8902

The plant vectors pMDO8902 was transformed into *Agrobacterium* and subsequently entered into plant transformation experiments, as previously described, to introduce the stacked genes into the maize genome. The selection agent for these experiments was glyphosate.

Western Blot Analysis

As before, the generated polyclonal antibodies were used in Western blots to determine if the transgenic protein was being expressed. At the T0 stage most icdh events were found to be expressing ICDH. Two events were promoted to the T1 stage and each of these had good expression levels.

Nitrogen Assays, T0 Events

A series of assays that quantify nitrogen intermediates in plants have been developed. These nitrogen assay methods are described in the previous section. Briefly, each of the plants was sampled (leaf) following 4 weeks of growth in soil in a greenhouse. These leaf samples were processed to determine their nitrate, asparagine, glutamine, aspartic acid, glutamic acid, ammonium, total amino acid, chlorophyll and total protein levels. Included alongside in the analysis were plants that were transformed with a construct containing only the glyphosate selectable marker (no icdh, nagk, genes) and are referred to as control "non-GOI" plants.

The T0 data is shown in Table 5.

TABLE 5

Nitrogen levels, ICDH + NAGK vs. non-GOI maize events, 4 weeks after transfer to soil

| Plant # | GOI | Aspartic Acid (µg/g) | Glutamic Acid (µg/g) | Asparagine (µg/g) | Glutamine (µg/g) | Total Chlorophyll (a + b) (mg/g) | Ammonium (µg/g) | Total Amino Acids (mg/g) | Total Protein (mg/g) |
|---|---|---|---|---|---|---|---|---|---|
| 15102 | ICDH + NAGK | 146.0 | 785.7 | 1230.0 | 1464.9 | 0.092 | 754.605 | 216.736 | 24.521 |
| 15103 | ICDH + NAGK | 187.1 | 372.6 | 973.5 | 3279.8 | 0.127 | 836.415 | 268.941 | 43.110 |
| 15104 | ICDH + NAGK | 318.6 | 905.9 | 2202.9 | 7399.3 | 0.370 | 1087.857 | 605.138 | 53.679 |
| 15105 | ICDH + NAGK | 264.6 | 1082.6 | 2941.9 | 11934.4 | 0.134 | 865.201 | 440.129 | 25.618 |
| 15106 | ICDH + NAGK | 194.3 | 438.0 | 1766.1 | 10241.0 | 0.144 | 724.948 | 390.051 | 43.614 |
| 15107 | ICDH + NAGK | 122.4 | 481.7 | 1683.7 | 7154.5 | 0.126 | 582.000 | 282.809 | 30.601 |
| 15108 | ICDH + NAGK | 222.0 | 27.8 | 1839.7 | 4568.3 | 0.152 | 700.611 | 295.594 | 35.903 |
| 15109 | ICDH + NAGK | 466.7 | 603.5 | 1699.4 | 8891.9 | 0.281 | 851.859 | 347.156 | 28.974 |
| 15110 | ICDH + NAGK | 124.8 | 475.6 | 996.7 | 6484.5 | 0.114 | 654.786 | 236.433 | 37.768 |
| IC 1 Control | non-GOI | 537.8 | 596.3 | 2335.0 | 3516.7 | 0.154 | 984.3 | 362.2 | 28.6 |
| IC 2 Control | non-GOI | 101.6 | 473.7 | 1490.3 | 2485.0 | 0.157 | 505.7 | 264.3 | 34.6 |
| IC 3 Control | non-GOI | 153.6 | 914.9 | 1799.3 | 2191.5 | 0.066 | 534.6 | 297.8 | 34.0 |
| IC 4 Control | non-GOI | 59.7 | 526.2 | 313.0 | 659.3 | 0.082 | 347.3 | 183.7 | 24.1 |
| Avg | | 213.2 | 627.8 | 1484.4 | 2213.1 | 0.114 | 593.0 | 277.0 | 30.3 |
| Std Dev | | 219.8 | 197.9 | 855.4 | 1181.5 | 0.048 | 273.6 | 74.3 | 5.0 |

Compared to the control (and standard deviation), one T0 event (15109) had higher levels of aspartic acid. Several events had higher glutamine levels, higher total amino acids and higher protein compared to the control. From these results the events 15105 (elevated Glu, Asp, Gln, total AAs) and 15106 (elevated Gln, total AAs, protein) were selected for T1 stage evaluations.

T1 Results

For each of the selected events, six T1 plants were produced, grown and sampled as described previously. Assays were performed and the results are shown in Table 6.

TABLE 6

Nitrogen levels, ICDH + NAGK vs. non-GOI maize events, 4 weeks after transfer to soil

| Plant # | GOI | Aspartic Acid (µg/g) | Glutamic Acid (µg/g) | Asparagine (µg/g) | Glutamine (µg/g) | Total Chlorophyll (a + b) (mg/g) | Ammonium (µg/g) | Total Amino Acids (mg/g) | Total Protein (mg/g) |
|---|---|---|---|---|---|---|---|---|---|
| 15105, #5 | ICDH + NAGK | 947 | 2789 | 1269 | 13837 | 0.544 | 930 | 555 | 18.7 |
| 15105, #13 | ICDH + NAGK | 827 | 1809 | 298 | 3163 | 0.312 | 619 | 339 | 22.0 |
| 15105, #14 | ICDH + NAGK | 430 | 1825 | 371 | 2818 | 0.384 | 611 | 511 | 17.6 |
| 15105, #15 | ICDH + NAGK | 785 | 3149 | 335 | 6217 | 0.214 | 460 | 423 | 21.7 |
| 15105, #17 | ICDH + NAGK | 274 | 1006 | 388 | 2632 | 0.609 | 425 | 368 | 19.9 |
| 15105, #18 | ICDH + NAGK | 453 | 2030 | 320 | 2523 | 0.233 | 485 | 247 | 17.1 |
| Avg | | 619 | 2101 | 497 | 5198 | 0.383 | 588 | 407 | 19.5 |
| Std Dev | | 442 | 766 | 380 | 4455 | 0.163 | 185 | 114 | 2.1 |
| 15106, #5 | ICDH + NAGK | 722 | 3797 | 3858 | 10471 | 0.674 | 963 | 425 | 17.9 |
| 15106, #9 | ICDH + NAGK | 184 | 2469 | 549 | 2556 | 0.279 | 600 | 260 | 13.9 |
| 15106, #10 | ICDH + NAGK | 373 | 1408 | 3319 | 10395 | 0.234 | 773 | 458 | 21.0 |
| 15106, #11 | ICDH + NAGK | 1463 | 4102 | 4382 | 9148 | 0.383 | 637 | 632 | 22.1 |
| 15106, #13 | ICDH + NAGK | 544 | 3437 | 3294 | 5693 | 0.223 | 884 | 416 | 23.3 |
| 15106, #17 | ICDH + NAGK | 591 | 2331 | 2790 | 5572 | 0.255 | 815 | 501 | 30.4 |
| Avg | | 646 | 2924 | 3032 | 7306 | 0.341 | 779 | 449 | 21.4 |
| Std Dev | | 442 | 1027 | 1333 | 3198 | 0.173 | 140 | 121 | 5.5 |
| Control 1 | | 253 | 2351 | 1759 | 2412 | 0.298 | 567 | 235 | 22.0 |
| Control 2 | | 739 | 2154 | 3488 | 3989 | 0.089 | 452 | 226 | 17.4 |
| Control 3 | | 297 | 1767 | 373 | 2532 | 0.107 | 408 | 197 | 21.2 |
| Control 4 | | 905 | 2233 | 941 | 3237 | 0.145 | 314 | 190 | 17.2 |
| Control 5 | | 394 | 3037 | 3346 | 5262 | 0.155 | 504 | 252 | 19.5 |
| Control 6 | | 789 | 2535 | 4166 | 9084 | 0.133 | 459 | 295 | 28.9 |
| Avg | | 563 | 2346 | 2346 | 4419 | 0.154 | 451 | 232 | 21.0 |
| Std Dev | | 281 | 424 | 1538 | 2516 | 0.074 | 86 | 38 | 4.3 |

Compared to the control average (and Standard Deviation), the averages showed that 15105 had lower asparagine, higher chlorophyll, and higher total amino acids; 15106 had higher glutamate, higher chlorophyll, and higher total amino acids.

Since the stack ICDH+NAGK appeared to have several positive effects, especially in the later nitrogen-containing metabolites (e.g. chlorophyll, total amino acids), we used previous data on NAGK effects (U.S. patent application Ser. No. 12/916,854, filed Nov. 1, 2010, and incorporated herein in its entirety by this reference) and compared that to ICDH alone and ICDH+NAGK. The results are shown in Table 7 (data are % of control).

TABLE 7

Data on NAGK Alone, ICDH Alone and ICDH + NAGK

|  | Aspartic Acid (µg/g) | Glutamic Acid (µg/g) | Asparagine (µg/g) | Glutamine (µg/g) | Total Chlorophyll (a + b) (mg/g) | Ammonium (µg/g) | Total Amino Acids (mg/g) | Total Protein (mg/g) |
|---|---|---|---|---|---|---|---|---|
| NAGK Alone | 162% | 155% | 191% | 140% | 90% | 120% | 124% | 105% |
| ICDH Alone | 105% | 111% | 18% | 65% | 131% | 102% | 98% | 87% |
| ICDH + NAGK | 112% | 107% | 75% | 141% | 234% | 152% | 184% | 97% |

We excluded the one plant (15125 #4) from the ICDH values since it seemed to be a high outlier. The results show a pattern where: (1) NAGK alone tends to impact the intermediate N-metabolites (Asp, Asn, Glu, Gln); (2) ICDH alone impacts chlorophyll; and (3) ICDH+NAGK shows impacts on chlorophyll and total amino acids. This stack effect indicates that N was assimilated and moved towards end-products to a greater extent than with either gene alone.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto. Those skilled in the art who have the disclosure before them will be able to make modifications and variations therein without departing from the scope of the invention.

SEQUENCE LISTING

SEQ ID NO: 1
ATGAGCACCCCCAAGATCATCTACACCTTGACAGATGAGGCGCCGGCGCT

GGCCACCTACAGCTTGCTGCCCATCATCAAGGCTTTCACTGGAAGCTCAG

GCATTGCTGTGGAAACAAGGGACATCTCCCTTGCTGGAAGGCTGATCGCC

ACCTTCCCAGAATATTTGACAGACACCCAGAAGATCTCTGATGATCTTGC

TGAGCTGGGGAAGCTGGCCACCACGCCAGATGCCAACATCATCAAGCTGC

CAAACATCTCTGCTTCAGTTCCTCAGCTGAAGGCCGCCATCAAGGAACTC

CAGCAGCAAGGCTACAAGCTGCCAGATTATCCAGAAGAACCAAAAACAGA

CACAGAGAAGGATGTCAAGGCAAGATATGACAAGATCAAGGGCAGCGCCG

TCAACCCCGTGCTGAGAGAAGGAAATTCAGACCGCCGCGCGCCGCTCTCC

GTCAAGAACTATGCAAGGAAGCATCCTCACAAGATGGGCGCCTGGAGCGC

CGACAGCAAGAGCCATGTTGCTCACATGGACAATGGAGATTTCTATGGAT

CAGAGAAGGCGGCGCTGATTGGTGCTCCTGGAAGCGTCAAGATTGAGCTG

ATCGCCAAGGATGGAAGCAGCACCGTGCTGAAGGCCAAGACATCAGTTCA

AGCTGGAGAGATCATCGACAGCTCCGTGATGAGCAAGAATGCTCTGAGGA

ACTTCATTGCTGCCGAGATTGAAGATGCCAAGAAGCAAGGAGTGCTGCTC

TCCGTCCACCTCAAGGCCACCATGATGAAGGTTTCAGATCCCATCATGTT

TGGCCAGATTGTTTCAGAGTTCTACAAGGATGCTCTCACCAAGCATGCTG

AGGTGCTGAAGCAGATTGGATTTGATGTCAACAATGGCATTGGAGATCTC

TATGCAAGGATCAAGACCCTACCAGAAGCAAAGCAGAAGGAGATTGAAGC

TGACATCCAAGCTGTTTATGCTCAAAGGCCGCAGCTGGCAATGGTGAACA

GCGACAAGGGCATCACCAACCTCCATGTTCCTTCTGATGTCATCGTCGAC

GCCTCCATGCCGGCCATGATCAGAGATTCAGGGAAGATGTGGGGGCCAGA

TGGCAAGCTGCATGACACCAAGGCCGTCATCCCAGATCGCTGCTATGCTG

GCGTCTACCAGGTGGTGATTGAAGATTGCAAGCAGCATGGCGCCTTCGAC

CCAACAACAATGGGCTCAGTTCCAAATGTTGGGCTGATGGCGCAGAAGGC

AGAAGAATATGGAAGCCATGACAAGACCTTTCAGATCCCTGCTGATGGCG

TCGTCCGCGTCACTGATGAAAGCGGCAAGCTGCTGCTGGAGCAATCAGTG

GAAGCTGGAGACATCTGGAGGATGTGCCAAGCAAAGGATGCTCCCATCCA

AGATTGGGTGAAGCTCGCCGTCAACAGGGCGCGCGCCACCAACACGCCGG

CGGTGTTCTGGCTGGACCCAGCAAGGGCTCATGATGCTCAGGTGATCGCC

AAGGTGGAGAGATATCTAAAGGATTATGACACCTCCGGCCTGGACATCAG

GATCTTGTCGCCGGTGGAAGCAACAAGGTTCTCCTTGGCAAGGATCAGAG

AAGGAAAGGACACCATCTCAGTGACAGGAAATGTGCTGAGGGACTACCTC

ACCGACCTCTTCCCCATCATGGAGCTGGGCACCTCCGCCAAGATGCTCTC

CATTGTTCCTCTGATGAGCGGCGGCGGCCTCTTTGAAACTGGAGCTGGAG

GATCAGCGCCCAAGCATGTTCAGCAGTTCCTGGAAGAAGGCTACCTCAGA

TGGGACAGCCTTGGAGAGTTCCTGGCGCTCGCCGCCTCCTTGGAGCATCT

TGGAAATGCCTACAAGAACCCAAAGGCGCTGGTGCTGGCCTCCACCCTAG

-continued

ATCAAGCTACTGGCAAGATCCTGGACAACAACAAGAGCCCAGCAAGGAAG

GTTGGTGAGATCGACAACAGAGGAAGCCACTTCTACCTGGCGCTCTACTG

GGCTCAAGCTCTTGCTGCTCAAACAGAGGACAAGGAGCTACAAGCTCAGT

TCACCGGCATTGCCAAGGCGCTGACAGACAATGAAACAAAAATTGTTGGA

GAGCTGGCTGCTGCTCAAGGAAAGCCGGTGGACATTGCTGGCTACTACCA

TCCAAACACCGACCTCACCAGCAAGGCCATCAGGCCATCTGCCACCTTCA

ATGCTGCTCTGGCGCCGCTGGCATAGTAAGG

SEQ ID NO: 2

MSTPKIIYTL TDEAPALATY SLLPIIKAFT GSSGIAVETR

DISLAGRLIA TFPEYLTDTQ KISDDLAELG KLATTPDANI

IKLPNISASV PQLKAAIKEL QQQGYKLPDY PEEPKTDTEK

DVKARYDKIK GSAVNPVLRE GNSDRRAPLS VKNYARKHPH

KMGAWSADSK SHVAHMDNGD FYGSEKAALI GAPGSVKIEL

IAKDGSSTVL KAKTSVQAGE IIDSSVMSKN ALRNFIAAEI

EDAKKQGVLL SVHLKATMMK VSDPIMFGQI VSEFYKDALT

KHAEVLKQIG FDVNNGIGDL YARIKTLPEA KQKEIEADIQ

AVYAQRPQLA MVNSDKGITN LHVPSDVIVD ASMPAMIRDS

GKMWGPDGKL HDTKAVIPDR CYAGVYQVVI EDCKQHGAFD

PTTMGSVPNV GLMAQKAEEY GSHDKTFQIP ADGVVRVTDE

SGKLLLEQSV EAGDIWRMCQ AKDAPIQDWV KLAVNRARAT

NTPAVFWLDP ARAHDAQVIA KVERYLKDYD TSGLDIRILS

PVEATRFSLA RIREGKDTIS VTGNVLRDYL TDLFPIMELG

TSAKMLSIVP LMSGGGLFET GAGGSAPKHV QQFLEEGYLR

WDSLGEFLAL AASLEHLGNA YKNPKALVLA STLDQATGKI

LDNNKSPARK VGEIDNRGSH FYLALYWAQA LAAQTEDKEL

QAQFTGIAKA LTDNETKIVG ELAAAQGKPV DIAGYYHPNT

DLTSKAIRPS ATFNAALAPL A

SEQ ID NO: 3
ATGCAGCTGCTCAACCAGCGGCAGGCGCTGCGGCTGGGAAGAAGCTCCGC

CAGCAAGAACCAGCAGGTGGCGCCGCTGGCATCAAGGCCGGCAAGCAGCC

TCTCCGTCTCCGCCTCCTCCGTGGCGCCGGCGCCGGCCTGCTCGGCGCCG

GCCGGCGCCGGCCGCCGCGCCGTGGTGGTGCGCGCCTCCGCCACCAAGGA

GAAGGTGGAGGAGCTCACCATCCAGATGCTGCATGAGGTGATGGTGATCA

AGTGCGGCGGCAGCATGCTGGAGCAGCTGCCGGAGAGCTTCTACAACAAG

CTGGCCGACGCTGCAAGCAGAAGGAAGAAGCATCGTCATTGTTCATGGAGG

AGGGCCGGCCATCAACCAGATGCTGGAGCAGCTGAAGATTGAGCCAACCT

TCTCAAATGGGCTGAGGGTGACAGATGAGCCAACAATGCAAGCTGTGGAG

ATGGTGCTCTCAGGGCCCATCAACAAGCTGGTGGTGAGGAAGCTGCTGCA

CGCCGGCGGCAAGGCATGGGGCCTCAGCGGCGTGGATGGAAGCCTGCTGC

AAGCTGTTGAGAAGACTCAAGGCCTCGGCCTGGTGGGCAGCATCACCGTG

GTGGATCAAGCGCCGCTCCAGCTGCTGCTGAGCAATGGCTACATCCCGGT

GGTGTCTCCCATCGCCGTCTCAGAAGATGGAAGAACAAGATACAACTGCA

ACGCCGACACCGTCGCCGGCGCCATTGCTTCAGCTCTCGGCGCCAAGCAG

CTGCTGATGCTCACTGATGTTCCTGGCATCTGGGCAGAAAATGAGCTGGG

AGAGAAGCAGCTGCTGCCGACGGTGACAACAGAAGATATTCAGCTGATGA

TGAAGAACCAGATCATCACCGGCGGCATGATCCCCAAGGTGCAAGCGGCG

CTGGATGCTCTAGCTCAAGGAGTTCAAGAAGTGGTGATCTGCAAAGGAGA

AGCTGAGACGCTGGACGGCGTGGTGAAGGGCATGGCCGTCGGCACCTCCA

TCTCCGCCGAGATGAGCAGAGGACAAGATTCTCAAGCCTTCATCAGCAAC

AAGGTGTGAGG

SEQ ID NO: 4:

MLHEVMVIKC GGSMLEQLPE SFYNKLATLQ AEGRSIVIVH

GGGPAINQML EQLKIEPTFS NGLRVTDEPT MQAVEMVLSG

PINKLVVRKL LHAGGKAWGL SGVDGSLLQA VEKTQGLGLV

GSITVVDQAP LQLLLSNGYI PVVSPIAVSE DGRTRYNCNA

DTVAGAIASA LGAKQLLMLT DVPGIWAENE LGEKQLLPTV

TTEDIQLMMK NQIITGGMIP KVQAALDALA QGVQEVVICK

GEAETLDGVV KGMAVGTSIS AEMSRGQDSQ AFISNKV

---

We claim:

1. A construct comprising a nucleotide sequence selected from the group consisting of:
   a) the nucleotide sequence SEQ ID NO: 1; and
   b) a nucleotide sequence encoding the amino acid sequence of SEQ ID NO: 2; and, operably linked to a heterologous 5' DNA plant promoter.

2. An expression vector comprising a nucleotide sequence selected from the group consisting of:
   a) the nucleotide sequence SEQ ID NO: 1; and
   b) a nucleotide sequence encoding the amino acid sequence of SEQ ID NO: 2;
   and an operably linked 5' DNA plant promoter sequence; wherein said nucleotide sequence modulates nitrogen use in a plant.

3. The expression vector according to claim 2, further comprising a 3' terminator sequence, wherein the nucleotide sequence, the DNA promoter sequence, and the terminator sequence are operatively coupled to permit transcription of the nucleotide sequence.

4. The expression vector according to claim 3, wherein the promoter sequence is selected from the group consisting of constitutive plant promoters and tissue specific promoters.

5. A plant, transformed with the construct of claim 1; wherein said nucleotide sequence modulates nitrogen use in a plant.

6. The plant according to claim 5, wherein the plant is selected from the group consisting of corn (maize); sorghum; wheat; sunflower; tomato; crucifers; peppers; potato; cotton; rice; soybean; sugarbeet; sugarcane; tobacco; barley; and oilseed rape; Brassica sp.; alfalfa; rye; millet; safflower; peanuts; sweet potato; cassava; coffee; coconut; pineapple; cocoa; tea; banana; avocado; fig; guava; mango; olive; papaya; cashew; macadamia; almond; oats; vegetables; grasses; vegetables, including but not limited to, onions, tomatoes, lettuce, green beans, lima beans, peas, and members of the genus Cucumis such as cucumber, cantaloupe, and muskmelon; ornamentals, including, but are not limited to, azalea, hydrangea, hibiscus, roses, tulips, daffodils, petunias, carnation, poinsettia, and chrysanthemum; pulp trees; oil palm; and conifers.

7. A component part of the plant of claim 6 that contains the construct, and further comprises a nucleotide sequence selected from the group consisting of: the nucleotide sequence SEQ ID NO: 3; and a nucleotide sequence encoding the amino acid sequence of SEQ ID NO: 4.

8. A plant seed produced from the plant of claim 6 that contains the construct, and further comprises a second nucleotide sequence selected from the group consisting of: the nucleotide sequence SEQ ID NO: 3; and a nucleotide sequence encoding the amino acid sequence of SEQ ID NO: 4.

9. A plant seed transformed with the vector of claim 2.

10. A host cell, transformed with the construct of claim 1; wherein said nucleotide sequence modulates nitrogen use in a plant.

11. The host cell of claim 10, wherein said host cell further comprises at least a second nucleotide sequence selected from the nucleotide sequences SEQ ID NO: 3 and a nucleotide sequence encoding the amino acid sequences of SEQ ID NO:4.

12. The host cell according to claim 10, wherein the host cell is selected from the group consisting of bacterial cells and plant cells.

13. A vector construct, comprising:
    a) a first nucleotide sequence encoding an amino acid sequence selected from the group consisting of:
       i) the nucleotide sequences SEQ ID NO: 1;
       ii) a nucleotide sequence encoding the amino acid sequence of SEQ ID NO: 2;
       wherein said nucleotide sequence modulates nitrogen use in a plant;
    b) a 5' DNA plant promoter sequence; and,
    c) a 3' terminator sequence, wherein the nucleotide sequence, the DNA promoter sequence, and the terminator sequence are operatively linked to permit transcription of the nucleotide sequence.

14. The vector construct according to claim 13, further comprising a second nucleotide sequence selected from the group consisting of: the nucleotide sequence SEQ ID NO: 3; and a nucleotide sequence encoding the amino acid sequence of SEQ ID NO: 4.

15. A method of expressing a nucleic acid molecule that modulates nitrogen in a plant, said method comprising the steps of providing a transgenic plant or plant seed transformed with a vector construct according to claim 2, and growing the transgenic plant or a plant grown from the transgenic plant seed under conditions effective to express the nucleic acid molecule in said transgenic plant or said plant grown from the transgenic plant seed.

16. The method according to claim 15, wherein expression of the nucleic acid molecule is effective in alleviating a limitation such that yield is increased in said transgenic plant or said plant grown from the transgenic plant seed.

17. The method according to claim 15, wherein expression of the nucleic acid molecule is effective in increasing efficiency of nitrogen utilization of said transgenic plant or said plant grown from the transgenic plant seed.

18. The method according to claim 15, wherein the plant is selected from the group consisting of corn (maize);

sorghum; wheat; sunflower; tomato; crucifers; peppers; potato; cotton; rice; soybean; sugarbeet; sugarcane; tobacco; barley; and oilseed rape; *Brassica* sp.; alfalfa; rye; millet; safflower; peanuts; sweet potato; cassava; coffee; coconut; pineapple; cocoa; tea; banana; avocado; fig; guava; mango; olive; papaya; cashew; macadamia; almond; oats; vegetables; grasses; vegetables, including but not limited to, onions, tomatoes, lettuce, green beans, lima beans, peas, and members of the genus *Cucumis* such as cucumber, cantaloupe, and muskmelon; ornamentals, including, but are not limited to, azalea, hydrangea, hibiscus, roses, tulips, daffodils, petunias, carnation, poinsettia, and chrysanthemum; pulp trees; oil palm; and conifers.

19. The method according to claim 15, wherein expression of the nucleic acid molecule is effective in improving the stress tolerance of said transgenic plant or said plant grown from the transgenic plant seed.

20. The method according to claim 15, wherein expression of the nucleic acid molecule is effective in altering the morphology of said transgenic plant or said plant grown from the transgenic plant seed.

21. A transgenic corn plant, comprising a corn plant transformed with a nucleotide sequence comprising a gene encoding a cytosolic ICDH enzyme and at least an NAGK gene that improve nitrogen utilization efficiency in corn wherein the transformed corn plant has increased chlorophyll over the starting corn plant.

22. A transgenic corn plant, comprising a corn plant transformed with a nucleotide sequence comprising a gene encoding a cytosolic ICDH enzyme and at least an nagk gene that improve nitrogen utilization efficiency in corn wherein the transformed corn plant has increased total amino acids over the starting corn plant.

23. A method of improving the grain number of a corn plant, comprising the steps of introducing into the genome of the plant a cytosolic icdh gene and an nagk gene that improves nitrogen utilization efficiency and growing the transformed plant to produce grain.

* * * * *

UNITED STATES PATENT AND TRADEMARK OFFICE
CERTIFICATE OF CORRECTION

PATENT NO. : 9,725,701 B2
APPLICATION NO. : 13/833247
DATED : August 8, 2017
INVENTOR(S) : McLaren et al.

It is certified that error appears in the above-identified patent and that said Letters Patent is hereby corrected as shown below:

In the Title:

There is a typo in the title. It should read: "A Prokaryotic-type Isocitrate Dehydrogenase and Its Application for Improving Nitrogen Utilization in Transgenic Plants"

Signed and Sealed this
Twenty-fourth Day of October, 2017

Joseph Matal
*Performing the Functions and Duties of the
Under Secretary of Commerce for Intellectual Property and
Director of the United States Patent and Trademark Office*

SEQUENCE LISTING

<160> NUMBER OF SEQ ID NOS: 4

<210> SEQ ID NO 1
<211> LENGTH: 2231
<212> TYPE: DNA
<213> ORGANISM: Artificial Sequence
<220> FEATURE:
<223> OTHER INFORMATION: synthetic construct

<400> SEQUENCE: 1
atgagcaccc ccaagatcat ctacaccttg acagatgagg cgccggcgct ggccacctac    60
agcttgctgc ccatcatcaa ggctttcact ggaagctcag gcattgctgt ggaaacaagg   120
gacatctccc ttgctggaag gctgatcgcc accttcccag aatatttgac agacacccag   180

```
aagatctctg atgatcttgc tgagctgggg aagctggcca ccacgccaga tgccaacatc    240
atcaagctgc caaacatctc tgcttcagtt cctcagctga aggccgccat caaggaactc    300
cagcagcaag gctacaagct gccagattat ccagaagaac aaaaacagac acagagaag    360 gatgtcaagg caagatatga caagatcaag ggcagcgccg tcaacccgt gctgagagaa     420 ggaaattcag accgccgcgc gccgctctcc gtcaagaact atgcaaggaa gcatcctcac    480
aagatgggcg cctggagcgc cgacagcaag agccatgttg ctcacatgga caatggagat    540
ttctatggat cagagaaggc ggcgctgatt ggtgctcctg aagcgtcaa gattgagctg     600 atcgccaagg atggaagcag caccgtgctg aaggccaaga catcagttca agctggagag    660
atcatcgaca gctccgtgat gagcaagaat gctctgagga acttcattgc tgccgagatt    720
gaagatgcca agaagcaagg agtgctgctc tccgtccacc tcaaggccac catgatgaag    780
gtttcagatc ccatcatgtt tggccagatt gtttcagagt tctacaagga tgctctcacc    840
aagcatgctg aggtgctgaa gcagattgga tttgatgtca acaatggcat tggagatctc    900
tatgcaagga tcaagaccct accagaagca aagcagaagg agattgaagc tgacatccaa    960 gctgttatg ctcaaaggcc gcagctggca atggtgaaca gcgacaaggg catcaccaac    1020
ctccatgttc cttctgatgt catcgtcgac gcctccatgc cggccatgat cagagattca    1080
gggaagatgt ggggccaga tggcaagctg catgacacca aggccgtcat cccagatcgc    1140
tgctatgctg gcgtctacca ggtggtgatt gaagattgca gcagcatgg cgccttcgac    1200 ccaacaacaa tgggctcagt tccaaatgtt gggctgatgg cgcagaaggc agaagaatat    1260
ggaagccatg acaagacctt tcagatccct gctgatggc tcgtccgcgt cactgatgaa    1320
agcggcaagc tgctgctgga gcaatcagtg gaagctggag acatctggag gatgtgccaa    1380
gcaaaggatg ctcccatcca agattgggtg aagctcgccg tcaacagggc gcgcgccacc    1440
aacacgccgg cggtgttctg gctggaccca gcaagggctc atgatgctca ggtgatcgcc    1500
aaggtggaga gatatctaaa ggattatgac acctccggcc tggacatcag gatcttgtcg    1560
ccggtggaag caacaaggtt ctccttggca aggatcagag aaggaaagga caccatctca    1620
gtgacaggaa atgtgctgag ggactacctc accgacctct tccccatcat ggagctgggc    1680
acctccgcca agatgctctc cattgttcct ctgatgagcg gcggcggcct ctttgaaact    1740
ggagctggag gatcagcgcc caagcatgtt cagcagttcc tggaagaagg ctacctcaga    1800
tgggacagcc ttggagagtt cctggcgctc gccgcctcct ggagcatct tggaaatgcc    1860 tacaagaacc caaaggcgct ggtgctggcc tccaccctag atcaagctac tggcaagatc    1920
ctggacaaca acaagagccc agcaaggaag gttggtgaga tcgacaacag aggaagccac    1980
ttctacctgg cgctctactg ggctcaagct cttgctgctc aaacagagga caaggagcta    2040
caagctcagt tcaccggcat tgccaaggcg ctgacagaca atgaaacaaa aattgttgga    2100
gagctggctg ctgctcaagg aaagccggtg acattgctg ctactacca tccaaacacc     2160 gacctcacca gcaaggccat caggccatct gccaccttca atgctgctct ggcgccgctg    2220
gcatagtaag g                                                         2231
```

<210> SEQ ID NO 2
<211> LENGTH: 741
<212> TYPE: PRT
<213> ORGANISM: Artificial Sequence
<220> FEATURE:
<223> OTHER INFORMATION: synthetic construct

<400> SEQUENCE: 2

-continued

```
Met Ser Thr Pro Lys Ile Ile Tyr Thr Leu Thr Asp Glu Ala Pro Ala
1               5                   10                  15
Leu Ala Thr Tyr Ser Leu Leu Pro Ile Ile Lys Ala Phe Thr Gly Ser
                20                  25                  30
Ser Gly Ile Ala Val Glu Thr Arg Asp Ile Ser Leu Ala Gly Arg Leu
            35                  40                  45
Ile Ala Thr Phe Pro Glu Tyr Leu Thr Asp Thr Gln Lys Ile Ser Asp
        50                  55                  60
Asp Leu Ala Glu Leu Gly Lys Leu Ala Thr Thr Pro Asp Ala Asn Ile
65                  70                  75                  80
Ile Lys Leu Pro Asn Ile Ser Ala Ser Val Pro Gln Leu Lys Ala Ala
                85                  90                  95
Ile Lys Glu Leu Gln Gln Gln Gly Tyr Lys Leu Pro Asp Tyr Pro Glu
            100                 105                 110
Glu Pro Lys Thr Asp Thr Glu Lys Asp Val Lys Ala Arg Tyr Asp Lys
        115                 120                 125
Ile Lys Gly Ser Ala Val Asn Pro Val Leu Arg Glu Gly Asn Ser Asp
130                 135                 140
Arg Arg Ala Pro Leu Ser Val Lys Asn Tyr Ala Arg Lys His Pro His
145                 150                 155                 160
Lys Met Gly Ala Trp Ser Ala Asp Ser Lys Ser His Val Ala His Met
                165                 170                 175
Asp Asn Gly Asp Phe Tyr Gly Ser Glu Lys Ala Ala Leu Ile Gly Ala
            180                 185                 190
Pro Gly Ser Val Lys Ile Glu Leu Ile Ala Lys Asp Gly Ser Ser Thr
        195                 200                 205
Val Leu Lys Ala Lys Thr Ser Val Gln Ala Gly Glu Ile Ile Asp Ser
210                 215                 220
Ser Val Met Ser Lys Asn Ala Leu Arg Asn Phe Ile Ala Ala Glu Ile
225                 230                 235                 240
Glu Asp Ala Lys Lys Gln Gly Val Leu Leu Ser Val His Leu Lys Ala
                245                 250                 255
Thr Met Met Lys Val Ser Asp Pro Ile Met Phe Gly Gln Ile Val Ser
            260                 265                 270
Glu Phe Tyr Lys Asp Ala Leu Thr Lys His Ala Glu Val Leu Lys Gln
        275                 280                 285
Ile Gly Phe Asp Val Asn Asn Gly Ile Gly Asp Leu Tyr Ala Arg Ile
        290                 295                 300
Lys Thr Leu Pro Glu Ala Lys Gln Lys Glu Ile Glu Ala Asp Ile Gln
305                 310                 315                 320
Ala Val Tyr Ala Gln Arg Pro Gln Leu Ala Met Val Asn Ser Asp Lys
                325                 330                 335
Gly Ile Thr Asn Leu His Val Pro Ser Asp Val Ile Asp Ala Ser
            340                 345                 350
Met Pro Ala Met Ile Arg Asp Ser Gly Lys Met Trp Gly Pro Asp Gly
        355                 360                 365
Lys Leu His Asp Thr Lys Ala Val Ile Pro Asp Arg Cys Tyr Ala Gly
        370                 375                 380
Val Tyr Gln Val Val Ile Glu Asp Cys Lys Gln His Gly Ala Phe Asp
385                 390                 395                 400
Pro Thr Thr Met Gly Ser Val Pro Asn Val Gly Leu Met Ala Gln Lys
                405                 410                 415
```

Ala Glu Glu Tyr Gly Ser His Asp Lys Thr Phe Gln Ile Pro Ala Asp
            420                 425                 430

Gly Val Val Arg Val Thr Asp Glu Ser Gly Lys Leu Leu Leu Glu Gln
        435                 440                 445

Ser Val Glu Ala Gly Asp Ile Trp Arg Met Cys Gln Ala Lys Asp Ala
    450                 455                 460

Pro Ile Gln Asp Trp Val Lys Leu Ala Val Asn Arg Ala Arg Ala Thr
465                 470                 475                 480

Asn Thr Pro Ala Val Phe Trp Leu Asp Pro Ala Arg Ala His Asp Ala
                485                 490                 495

Gln Val Ile Ala Lys Val Glu Arg Tyr Leu Lys Asp Tyr Asp Thr Ser
            500                 505                 510

Gly Leu Asp Ile Arg Ile Leu Ser Pro Val Glu Ala Thr Arg Phe Ser
        515                 520                 525

Leu Ala Arg Ile Arg Glu Gly Lys Asp Thr Ile Ser Val Thr Gly Asn
    530                 535                 540

Val Leu Arg Asp Tyr Leu Thr Asp Leu Phe Pro Ile Met Glu Leu Gly
545                 550                 555                 560

Thr Ser Ala Lys Met Leu Ser Ile Val Pro Leu Met Ser Gly Gly Gly
                565                 570                 575

Leu Phe Glu Thr Gly Ala Gly Gly Ser Ala Pro Lys His Val Gln Gln
            580                 585                 590

Phe Leu Glu Glu Gly Tyr Leu Arg Trp Asp Ser Leu Gly Glu Phe Leu
        595                 600                 605

Ala Leu Ala Ala Ser Leu Glu His Leu Gly Asn Ala Tyr Lys Asn Pro
    610                 615                 620

Lys Ala Leu Val Leu Ala Ser Thr Leu Asp Gln Ala Thr Gly Lys Ile
625                 630                 635                 640

Leu Asp Asn Asn Lys Ser Pro Ala Arg Lys Val Gly Glu Ile Asp Asn
                645                 650                 655

Arg Gly Ser His Phe Tyr Leu Ala Leu Tyr Trp Ala Gln Ala Leu Ala
            660                 665                 670

Ala Gln Thr Glu Asp Lys Glu Leu Gln Ala Gln Phe Thr Gly Ile Ala
        675                 680                 685

Lys Ala Leu Thr Asp Asn Glu Thr Lys Ile Val Gly Glu Leu Ala Ala
    690                 695                 700

Ala Gln Gly Lys Pro Val Asp Ile Ala Gly Tyr Tyr His Pro Asn Thr
705                 710                 715                 720

Asp Leu Thr Ser Lys Ala Ile Arg Pro Ser Ala Thr Phe Asn Ala Ala
                725                 730                 735

Leu Ala Pro Leu Ala
            740

<210> SEQ ID NO 3
<211> LENGTH: 1061
<212> TYPE: DNA
<213> ORGANISM: Artificial Sequence
<220> FEATURE:
<223> OTHER INFORMATION: synthetic construct

<400> SEQUENCE: 3
atgcagctgc tcaaccagcg gcaggcgctg cggctgggaa gaagctccgc cagcaagaac      60
cagcaggtgg cgccgctggc atcaaggccg gcaagcagcc tctccgtctc cgcctcctcc     120
gtggcgccgg cgccggcctg ctcggcgccg gccggcgccg ccgccgcgc cgtggtggtg     180

```
cgcgcctccg ccaccaagga gaaggtggag gagctcacca tccagatgct gcatgaggtg    240
atggtgatca agtgcggcgg cagcatgctg gagcagctgc cggagagctt ctacaacaag    300
ctggcgacgc tgcaagcaga aggaagaagc atcgtcattg ttcatggagg agggccggcc    360
atcaaccaga tgctggagca gctgaagatt gagccaacct tctcaaatgg gctgagggtg    420
acagatgagc caacaatgca agctgtggag atggtgctct cagggcccat caacaagctg    480
gtggtgagga agctgctgca cgccggcggc aaggcatggg gcctcagcgg cgtggatgga    540
agcctgctgc aagctgttga gaagactcaa ggcctcggcc tggtgggcag catcaccgtg    600
gtggatcaag cgccgctcca gctgctgctg agcaatggct acatcccggt ggtgtctccc    660
atcgccgtct cagaagatgg aagaacaaga tacaactgca acgccgacac cgtcgccggc    720
gccattgctt cagctctcgg cgccaagcag ctgctgatgc tcactgatgt tcctggcatc    780
tgggcagaaa atgagctggg agagaagcag ctgctgccga cggtgacaac agaagatatt    840
cagctgatga tgaagaacca gatcatcacc ggcggcatga tccccaaggt gcaagcggcg    900
ctggatgctc tagctcaagg agttcaagaa gtggtgatct gcaaaggaga agctgagacg    960
ctggacggcg tggtgaaggg catggccgtc ggcacctcca tctccgccga tgagcaga    1020 ggacaagatt ctcaagcctt catcagcaac aaggtgtgag g                       1061
```

<210> SEQ ID NO 4
<211> LENGTH: 277
<212> TYPE: PRT
<213> ORGANISM: Artificial Sequence
<220> FEATURE:
<223> OTHER INFORMATION: synthetic construct

<400> SEQUENCE: 4

```
Met Leu His Glu Val Met Val Ile Lys Cys Gly Gly Ser Met Leu Glu
1               5                   10                  15

Gln Leu Pro Glu Ser Phe Tyr Asn Lys Leu Ala Thr Leu Gln Ala Glu
            20                  25                  30

Gly Arg Ser Ile Val Ile Val His Gly Gly Gly Pro Ala Ile Asn Gln
        35                  40                  45

Met Leu Glu Gln Leu Lys Ile Glu Pro Thr Phe Ser Asn Gly Leu Arg
    50                  55                  60

Val Thr Asp Glu Pro Thr Met Gln Ala Val Glu Met Val Leu Ser Gly
65                  70                  75                  80

Pro Ile Asn Lys Leu Val Val Arg Lys Leu Leu His Ala Gly Gly Lys
                85                  90                  95

Ala Trp Gly Leu Ser Gly Val Asp Gly Ser Leu Leu Gln Ala Val Glu
            100                 105                 110

Lys Thr Gln Gly Leu Gly Leu Val Gly Ser Ile Thr Val Val Asp Gln
        115                 120                 125

Ala Pro Leu Gln Leu Leu Leu Ser Asn Gly Tyr Ile Pro Val Val Ser
    130                 135                 140

Pro Ile Ala Val Ser Glu Asp Gly Arg Thr Arg Tyr Asn Cys Asn Ala
145                 150                 155                 160

Asp Thr Val Ala Gly Ala Ile Ala Ser Ala Leu Gly Ala Lys Gln Leu
                165                 170                 175

Leu Met Leu Thr Asp Val Pro Gly Ile Trp Ala Glu Asn Glu Leu Gly
            180                 185                 190

Glu Lys Gln Leu Leu Pro Thr Val Thr Thr Glu Asp Ile Gln Leu Met
        195                 200                 205
```

```
Met Lys Asn Gln Ile Ile Thr Gly Gly Met Ile Pro Lys Val Gln Ala
    210             215             220
Ala Leu Asp Ala Leu Ala Gln Gly Val Gln Glu Val Val Ile Cys Lys
225             230             235             240
Gly Glu Ala Glu Thr Leu Asp Gly Val Val Lys Gly Met Ala Val Gly
                245             250             255
Thr Ser Ile Ser Ala Glu Met Ser Arg Gly Gln Asp Ser Gln Ala Phe
            260             265             270
Ile Ser Asn Lys Val
            275
```